United States Patent
Fan et al.

(10) Patent No.: US 10,450,274 B2
(45) Date of Patent: Oct. 22, 2019

(54) QUINOLINE COMPOUNDS, PREPARATION METHODS THEREOF, AND USES THEREOF AS URATE TRANSPORTER INHIBITOR DRUG

(71) Applicant: HINOVA PHARMACEUTICALS INC., Chengdu, Sichuan (CN)

(72) Inventors: Lei Fan, Sichuan (CN); Wu Du, Sichuan (CN); Xinghai Li, Sichuan (CN); Yuanwei Chen, Sichuan (CN); Kexin Xu, Sichuan (CN); Ke Chen, Sichuan (CN); Shaohua Zhang, Sichuan (CN); Tongchuan Luo, Sichuan (CN)

(73) Assignee: HINOVA PHARMACEUTICALS INC., Chengdu, Sichuan (CN)

( * ) Notice: Subject to any disclaimer, the term of this patent is extended or adjusted under 35 U.S.C. 154(b) by 0 days.

(21) Appl. No.: 15/781,997

(22) PCT Filed: Dec. 6, 2016

(86) PCT No.: PCT/CN2016/108688
§ 371 (c)(1),
(2) Date: Jun. 6, 2018

(87) PCT Pub. No.: WO2017/097182
PCT Pub. Date: Jun. 15, 2017

(65) Prior Publication Data
US 2018/0362466 A1    Dec. 20, 2018

(30) Foreign Application Priority Data
Dec. 7, 2015   (CN) ............................ 2015 1 0896887

(51) Int. Cl.
| C07D 215/36 | (2006.01) |
| A61K 31/47 | (2006.01) |
| A61K 31/4709 | (2006.01) |
| C07D 401/04 | (2006.01) |
| C07D 401/12 | (2006.01) |

(52) U.S. Cl.
CPC ............ *C07D 215/36* (2013.01); *A61K 31/47* (2013.01); *A61K 31/4709* (2013.01); *C07D 401/04* (2013.01); *C07D 401/12* (2013.01)

(58) Field of Classification Search
CPC .. C07D 215/36; C07D 401/04; C07D 401/12; A61K 31/47; A61K 31/4709
See application file for complete search history.

(56) References Cited

U.S. PATENT DOCUMENTS

| 2,568,037 | A | * | 9/1951 | Surrey | ................. | C07D 215/26 544/128 |
| 9,637,484 | B2 | * | 5/2017 | Peng | ..................... | C07C 323/62 |

FOREIGN PATENT DOCUMENTS

| CN | 103068801 A |   | 4/2013 |
| EP | 1820515 A1 |   | 8/2007 |
| WO | 2014183555 | * | 11/2014 |
| WO | 2014183555 A1 |   | 11/2014 |

OTHER PUBLICATIONS

Gogte, CA 80:108425, abstract only of Indian J Chem, 11(11), 1115-1118, 1973. (Year: 1973).*
Levillain, CA123:9308, abstract only of Synthesis, vol. 1, 56-63, 1995. (Year: 1995).*
Patel, CA161:698629, abstract only of Current Org Synthesis, 11(4), 621-625, 2014. (Year: 2014).*
American Chemical Society ACS. Registry Database, Aug. 31, 2016 (Aug. 31, 2016) RN 1983708-93-5.
American Chemical Society ACS. Registry Database, Aug. 12, 2016 (Aug. 12, 2016) RN 1972499-87-8.
American Chemical Society ACS. Registry Database, Jun. 21, 2015 (Jun. 21, 2015) RN 1783, .43.5552 RN 1789, .52.2341 RN 1553, .71.7666 RN 1244, .09.9256 RN 1175, A2.2285 RN 1176, .68.1927 RN 1171, .04.1598 RN 1177, .13.0802 RN 1178, .80.0652 RN 1137, .09.3123 RN 1088, .25.3202 RN 878, .46.4766 RN 876, .71.4765 RN 100, .82.0727 RN 95, .32.1137 RN 5450-23-7.
American Chemical Society ACS. Registry Database, Feb. 13, 2014 (Feb. 13, 2014) RN 1542983-23-2.

* cited by examiner

*Primary Examiner* — D Margaret M Seaman
(74) *Attorney, Agent, or Firm* — Novick, Kim & Lee, PLLC; Allen Xue

(57) ABSTRACT

Quinoline compounds and salts, hydrates or solvates serving as a selective uric acid reabsorption inhibitor, can be used in the treatment of hyperuricemia and gout by promoting uric acid to excrete from the body and reducing serum uric acid. Such compounds have the effect of reducing the uric acid in the animal body and human body.

13 Claims, No Drawings

QUINOLINE COMPOUNDS, PREPARATION METHODS THEREOF, AND USES THEREOF AS URATE TRANSPORTER INHIBITOR DRUG

TECHNICAL FIELD

The present invention relates to quinoline compounds, preparation methods thereof, and uses thereof as urate transporter inhibitor drug.

BACKGROUND ART

Urate transporter (URAT1) inhibitor drugs are used for treatment of hyperuricemia, gout and other diseases.

CONTENT OF INVENTION

The present invention provides a kind of quinoline compounds, as well as uses thereof as urate transporter inhibitor drug.

The present invention provides compounds of formula (A) or optical isomers or solvates or chemically acceptable salts or pro-drugs thereof,

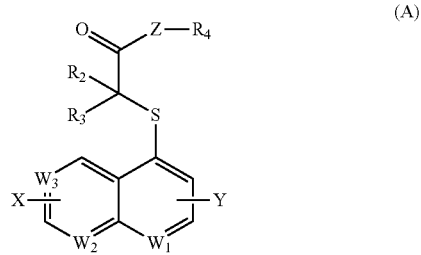

(A)

Wherein,
Z is selected from O, S or —NH—;
$W_1$ is selected from N or $CR^a$; $W_2$ is selected from N or $CR^b$; $W_3$ is selected from N or $CR^c$;
$R^a$, $R^b$, $R^c$, $R_2$ and $R_3$ are independently selected from the group of hydrogen, halogen, cyano, nitro, alkyl, alkenyl, alkynyl, cycloalkyl, heterocyclic radical, aryl, heteroaryl, —$OR^d$, —$S(O)_mR^d$, —$C(O)R^d$, $C(O)OR^d$, —$C(O)NR^eR^f$, —$NR^eR^f$ or $NR^eC(O)R^f$, respectively, wherein said alkyl, alkenyl, alkynyl, cycloalkyl, heterocyclic radical, aryl, or heteroaryl are independently and optionally further substituted by one or more substituents that are selected from the group of halogen, cyano, nitro, oxo-, alkyl, haloalkyl, hydroxyalkyl, alkenyl, alkynyl, cycloalkyl, heterocyclic radical, aryl, heteroaryl, —$OR^d$, —$S(O)_mR^d$, —$C(O)R^d$, $C(O)OR^d$, —$C(O)NR^eR^f$, —$NR^eR^f$ or $NR^eC(O)R^f$, respectively;
$R^d$ is selected from the group of hydrogen, halogen, alkyl, cycloalkyl, heterocyclic radical, aryl or heteroaryl, wherein said alkyl, cycloalkyl, heterocyclic radical, aryl, or heteroaryl is independently and optionally further substituted by one or more substituents that are selected from the group of halogen, cyano, nitro, hydroxyl, oxo-, alkyl, haloalkyl, hydroxyalkyl, alkoxy, cycloalkyl, heterocyclic radical, aryl, heteroaryl, carboxyl, carboxylic ester, —$C(O)NR^eR^f$, —$NR^eR^f$ or $NR^eC(O)R^f$, respectively;
$R^e$, $R^f$ are independently selected from the group of hydrogen, alkyl, cycloalkyl, heterocyclic radical, aryl or heteroaryl, respectively, wherein said alkyl, cycloalkyl, heterocyclic radical, aryl or heteroaryl are independently and optionally further substituted by one or more substituents selected from the group of halogen, cyano, nitro, hydroxyl, oxo-, alkyl, haloalkyl, hydroxyalkyl, alkoxy, cycloalkyl, heterocyclic radical, aryl, heteroaryl, carboxyl, carboxylic ester group, respectively; and m is 0, 1 or 2;
X, Y are independently selected from the group of hydrogen, halogen, cyano, nitro, alkyl, cycloalkyl, haloalkyl or hydroxyalkyl, respectively;
When Z is selected from O or S; $R_4$ is selected from hydrogen or $C_1$-$C_6$ alkyl, cycloalkyl, wherein said alkyl and cycloalkyl are independently and optionally substituted by one or more substituents selected from halogen, cyano, nitro, hydroxyl, oxo-, alkyl, haloalkyl, hydroxyalkyl, alkoxy, cycloalkyl, heterocyclic radical, aryl, heteroaryl, carboxyl, carboxylic ester group, —$C(O)NR^eR^f$, —$NR^eR^f$ or $NR^eC(O)R^f$; when Z is selected from —NH—, $R_4$ is selected from hydrogen, aryl or heteroaryl, and pyridyl is preferable.

Further, the compounds or optical isomers or solvates or chemically acceptable salts or pro-drugs thereof, the compounds have the structure of formula (I):

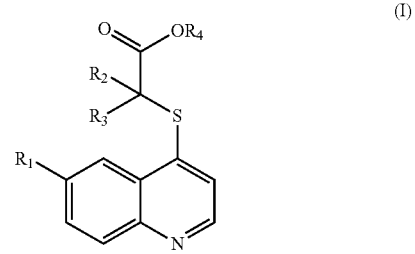

(I)

Wherein, $R_1$ is selected from hydrogen, halogen, trifluoromethyl, cyano, nitro, alkyl, alkenyl, alkynyl, cycloalkyl, heterocyclic radical, aryl, heteroaryl, —$OR^d$, —$S(O)_mR^d$, —$C(O)R^d$, $C(O)OR^d$, —$C(O)NR^eR^f$, —$NR^eR^f$ or $NR^eC(O)R^f$, in which said alkyl, alkenyl, alkynyl, cycloalkyl, heterocyclic radical, aryl or heteroaryl are independently and optionally further substituted by one or more substituents selected from halogen, cyano, nitro, oxo, alkyl, haloalkyl, hydroxyalkyl, alkenyl, alkynyl, cycloalkyl, heterocyclic radical, aryl, heteroaryl, —$OR^d$, —$S(O)_mR^d$, —$C(O)R^d$, $C(O)OR^d$, —$C(O)NR^eR^f$, —$NR^eR^f$ or $NR^eC(O)R^f$;
$R_2$, $R_3$, $R_4$, $R^d$, $R^e$, $R^f$, and m all have the same meaning as that in formula (A). Further, the compounds or optical isomers or solvates or chemically acceptable salts or pro-drugs thereof, wherein
$R_1$ is selected from the group of halogen, trifluoromethyl, substituted or unsubstituted alkyl, substituted or unsubstituted aryl, substituted or unsubstituted heteroaryl, and substituted or unsubstituted cycloalkyl.
$R_2$ and $R_3$ are independently selected from the group of hydrogen, halogen, substituted or unsubstituted alkyl, substituted or unsubstituted aryl, substituted or unsubstituted heteroaryl, and substituted or unsubstituted cycloalkyl, respectively.
$R_4$ is selected from the group of hydrogen or $C_1$-$C_6$ alkyl, $C_3$-$C_6$ cycloalkyl.
Further, the compounds or optical isomers or solvates or chemically acceptable salts or pro-drugs thereof, in which when Z is O, $R_4$ is selected from hydrogen.
Further, the compounds or optical isomers or solvates or chemically acceptable salts or pro-drugs thereof, in which $R_1$ is selected from the group of halogen, trifluoromethyl, substituted or unsubstituted aryl, substituted or unsubstituted pyridyl, substituted or unsubstituted pyrimidinyl, substituted or unsubstituted pyrrolyl, substituted or unsubstituted imidazolyl, substituted or unsubstituted furyl, substituted or unsubstituted thienyl, substituted or unsubstituted oxazolyl, substituted or unsubstituted thiazolyl, substituted or unsubstituted oxdiazolyl, substituted or unsubstituted thiadiazolyl or $C_3$-$C_6$ cycloalkyl.

Further, the compounds or optical isomers or solvates or chemically acceptable salts or pro-drugs thereof, $R_1$ is selected from the group of F, Br, Cl, tpyridyl, pyrimidinyl, pyrrolyl, imidazolyl, phenyl, trifluoromethyl or cyclopropyl, wherein said phenyl is optionally further substituted by one or more substituents selected from the group of methoxy, ethoxy, fluorine, chlorine, bromine or trifluoromethyl.

Further, the compounds or optical isomers or solvates or chemically acceptable salts or pro-drugs thereof, in which $R_2$ and $R_3$ are independently selected from hydrogen, halogen or $C_1$-$C_6$ alkyl, respectively.

Further, the compounds or optical isomers or solvates or chemically acceptable salts or pro-drugs thereof, in which $R_2$ is selected from hydrogen and $R_3$ is selected from methyl; or $R_2$ is selected from hydrogen and $R_3$ is selected from ethyl; or $R_2$ is selected from hydrogen and $R_3$ is selected from isopropyl; or $R_2$ and $R_3$ are both selected from methyl; or $R_2$ and $R_3$ are both selected from ethyl; or $R_2$ and $R_3$ are both selected from n-propyl.

Further, the compounds or optical isomers or solvates or chemically acceptable salts or pro-drugs thereof, the compounds have the structure of formula (Ia):

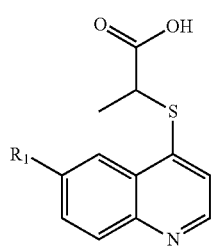

(Ia)

Wherein, $R_1$ has the meaning mentioned in claim 2.

Further, the compounds or optical isomers or solvates or chemically acceptable salts or pro-drugs thereof, wherein $R_1$ is selected from the group of halogen, trifluoromethyl, substituted or unsubstituted aryl, substituted or unsubstituted pyridyl, substituted or unsubstituted pyrimidinyl, substituted or unsubstituted pyrrolyl, substituted or unsubstituted imidazolyl, substituted or unsubstituted furyl, substituted or unsubstituted thienyl, substituted or unsubstituted oxazolyl, substituted or unsubstituted thiazolyl, substituted or unsubstituted oxdiazolyl, substituted or unsubstituted thiadiazolyl or $C_3$-$C_6$ cycloalkyl.

Further, the compounds or optical isomers or solvates or chemically acceptable salts or pro-drugs thereof, wherein, $R_1$ is selected from the group of F, Br, Cl, trifluoromethyl, pyridyl, pyrimidinyl, pyrrolyl, imidazolyl, phenyl or cyclopropyl, wherein said phenyl is optionally further substituted by one or more substituents selected from methoxy, ethoxy, fluorine, chlorine, bromine or trifluoromethyl.

Further, the compounds or optical isomers or solvates or chemically acceptable salts or pro-drugs thereof, the compounds have the structure of formula (Ib):

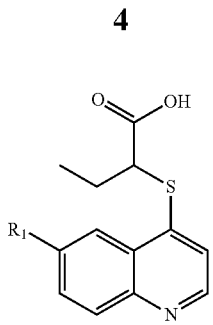

(Ib)

Wherein, $R_1$ has the meaning mentioned in claim 2.

Further, the compounds or optical isomers or solvates or chemically acceptable salts or pro-drugs thereof, wherein $R_1$ is selected from the group of halogen, trifluoromethyl, substituted or unsubstituted aryl, substituted or unsubstituted pyridyl, substituted or unsubstituted pyrimidinyl, substituted or unsubstituted pyrrolyl, substituted or unsubstituted imidazolyl, substituted or unsubstituted furyl, substituted or unsubstituted thienyl, substituted or unsubstituted oxazolyl, substituted or unsubstituted thiazolyl, substituted or unsubstituted oxdiazolyl, substituted or unsubstituted thiadiazolyl or $C_3$-$C_6$ cycloalkyl.

Further, the compounds or optical isomers or solvates or chemically acceptable salts or pro-drugs thereof, wherein, $R_1$ is selected from the group of F, Br, Cl, trifluoromethyl, pyridyl, pyrimidinyl, pyrrolyl, imidazolyl, phenyl or cyclopropyl, wherein said phenyl is optionally further substituted by one or more substituents selected from methoxy, ethoxy, fluorine, chlorine, bromine or trifluoromethyl.

Further, the compounds or optical isomers or solvates or chemically acceptable salts or pro-drugs thereof, the compounds have the structure of formula (Ic):

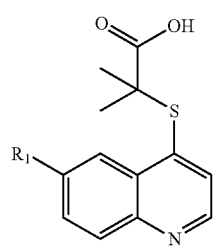

(Ic)

Wherein, $R_1$ has the meaning mentioned in claim 2.

Further, the compounds or optical isomers or solvates or chemically acceptable salts or pro-drugs thereof, wherein $R_1$ is selected from the group of halogen, trifluoromethyl, substituted or unsubstituted aryl, substituted or unsubstituted pyridyl, substituted or unsubstituted pyrimidinyl, substituted or unsubstituted pyrrolyl, substituted or unsubstituted imidazolyl, substituted or unsubstituted furyl, substituted or unsubstituted thienyl, substituted or unsubstituted oxazolyl, substituted or unsubstituted thiazolyl, substituted or unsubstituted oxdiazolyl, substituted or unsubstituted thiadiazolyl or $C_3$-$C_6$ cycloalkyl.

Further, the compounds or optical isomers or solvates or chemically acceptable salts or pro-drugs thereof, wherein, $R_1$ is selected from the group of F, Br, Cl, trifluoromethyl, pyridyl, pyrimidinyl, pyrrolyl, imidazolyl, phenyl or cyclopropyl, wherein said phenyl is optionally further substituted by one or more substituents selected from methoxy, ethoxy, fluorine, chlorine, bromine or trifluoromethyl.

Further, the compounds or optical isomers or solvates or chemically acceptable salts or pro-drugs thereof, the compounds have the structures of formula (Id) or (Ie).

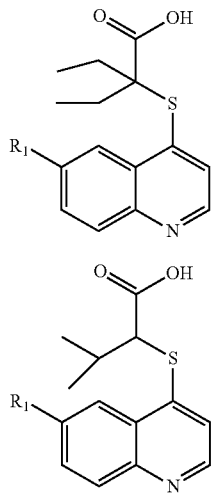

Wherein, $R_1$ has the meaning mentioned in claim 2.

Further, the compounds or optical isomers or solvates or chemically acceptable salts or pro-drugs thereof, wherein $R_1$ is selected from the group of halogen, trifluoromethyl, substituted or unsubstituted aryl, substituted or unsubstituted pyridyl, substituted or unsubstituted pyrimidinyl, substituted or unsubstituted pyrrolyl, substituted or unsubstituted imidazolyl, substituted or unsubstituted furyl, substituted or unsubstituted thienyl, substituted or unsubstituted oxazolyl, substituted or unsubstituted thiazolyl, substituted or unsubstituted oxdiazolyl, substituted or unsubstituted thiadiazolyl or $C_3$-$C_6$ cycloalkyl.

Further, the compounds or optical isomers or solvates or chemically acceptable salts or pro-drugs thereof, wherein, $R_1$ is selected from the group of F, Br, Cl, trifluoromethyl, pyridyl, pyrimidinyl, pyrrolyl, imidazolyl, phenyl or cyclopropyl, wherein said phenyl is optionally further substituted by one or more substituents selected from methoxy, ethoxy, fluorine, chlorine, bromine or trifluoromethyl.

Further, the compounds or optical isomers or solvates or chemically acceptable salts or pro-drugs thereof, wherein, $R_1$ is selected from cyclopropyl, and $R_2$ and $R_3$ both have the meaning mentioned in formula (A).

Further, the compounds or optical isomers or solvates or chemically acceptable salts or pro-drugs thereof, wherein, $R_2$ and $R_3$ are independently selected from hydrogen, halogen or $C_1$-$C_6$ alkyl, respectively.

Further, the compounds or optical isomers or solvates or chemically acceptable salts or pro-drugs thereof, wherein, $R_1$ is selected from pyridyl, and $R_2$ and $R_3$ both have the meaning mentioned in formula (A).

Further, the compounds or optical isomers or solvates or chemically acceptable salts or pro-drugs thereof, wherein, $R_2$ and $R_3$ are independently selected from hydrogen, halogen or $C_1$-$C_6$ alkyl.

Further, the compounds or optical isomers or solvates or chemically acceptable salts or pro-drugs thereof, wherein, $R_1$ is selected from phenyl substituted by one or two methoxy groups, and $R_2$ and $R_3$ both have the meaning mentioned in formula (A).

Further, the compounds or optical isomers or solvates or chemically acceptable salts or pro-drugs thereof, wherein, $R_2$ and $R_3$ are independently selected from hydrogen, halogen or $C_1$-$C_6$ alkyl, respectively.

Further, the compounds or optical isomers or solvates or chemically acceptable salts or pro-drugs thereof, wherein, $R_1$ is selected from Br, and $R_2$ and $R_3$ both have the meaning mentioned in formula (A).

Further, the compounds or optical isomers or solvates or chemically acceptable salts or pro-drugs thereof, wherein, $R_2$ and $R_3$ are independently selected from hydrogen, halogen or $C_1$-$C_6$ alkyl.

Further, the compounds or optical isomers or solvates or chemically acceptable salts or pro-drugs thereof, wherein, $R_1$ is selected from fluorophenyl, and $R_2$ and $R_3$ both have the meaning mentioned in formula (A).

Further, the compounds or optical isomers or solvates or chemically acceptable salts or pro-drugs thereof, wherein, $R_2$ and $R_3$ are independently selected from hydrogen, halogen or $C_1$-$C_6$ alkyl.

Further, the compounds or optical isomers or solvates or chemically acceptable salts or pro-drugs thereof, wherein, $R_1$ is selected from trifluoromethylphenyl, and $R_2$ and $R_3$ both have the meaning mentioned in formula (A).

Further, the compounds or optical isomers or solvates or chemically acceptable salts or pro-drugs thereof, wherein, $R_2$ and $R_3$ are independently selected from hydrogen, halogen or $C_1$-$C_6$ alkyl.

Further, the compounds or optical isomers or solvates or chemically acceptable salts or pro-drugs thereof, the compound is one of the following compounds:

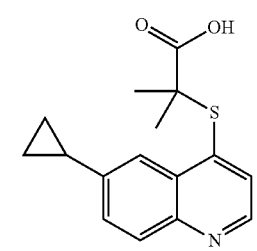

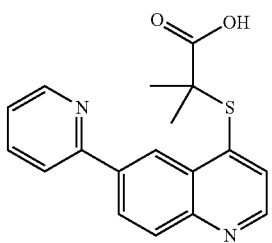

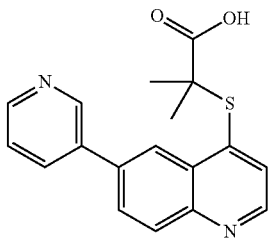

US 10,450,274 B2

-continued

| | |
|---|---|
| 24 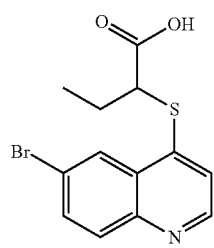 | 30 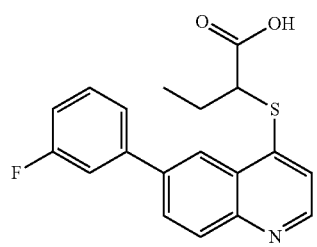 |
| 25 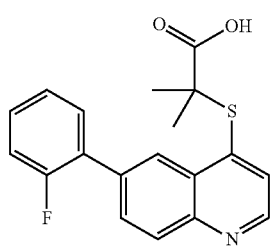 | 31 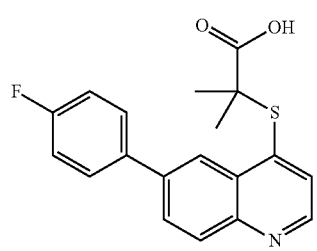 |
| 26 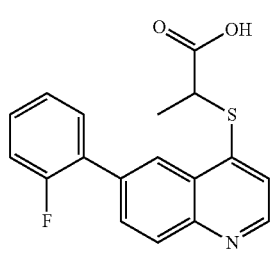 | 32 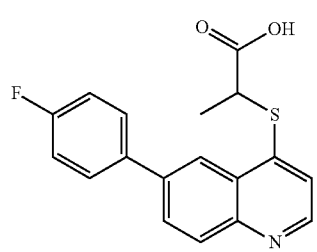 |
| 27 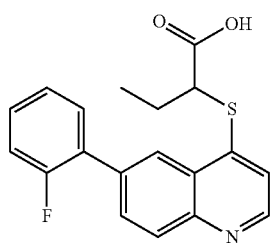 | 33 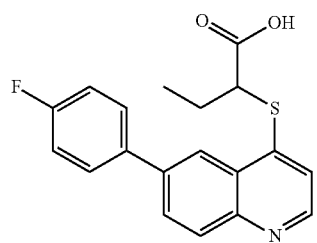 |
| 28 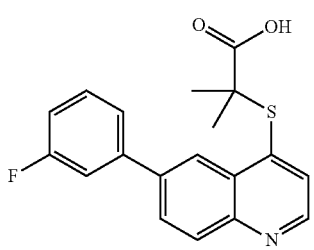 | 34 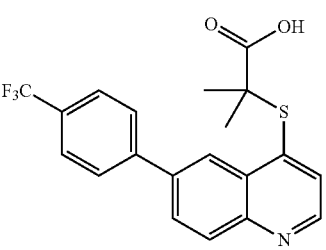 |
| 29 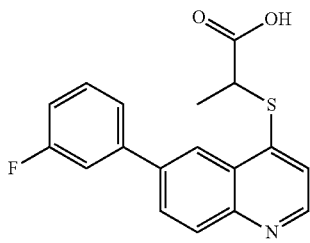 | 35 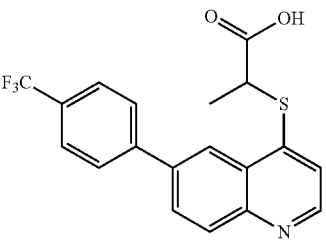 |

92 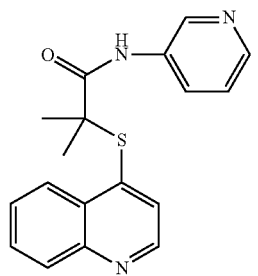
93 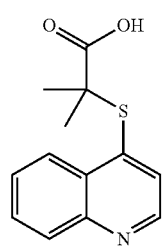
94 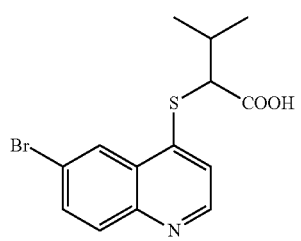
95 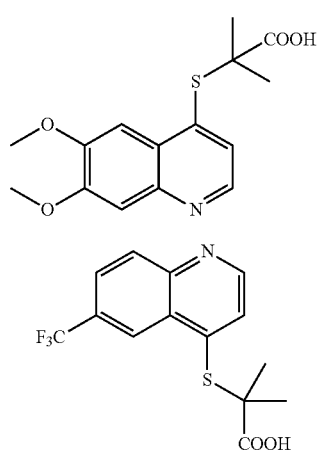
96 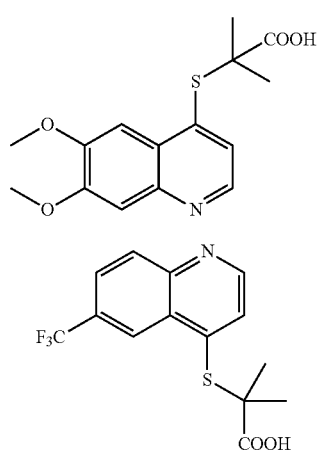
100 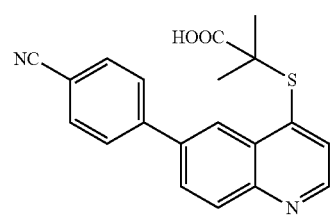
101 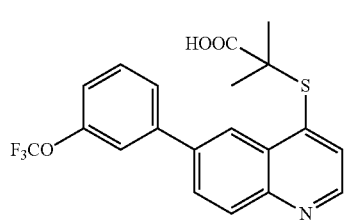
102 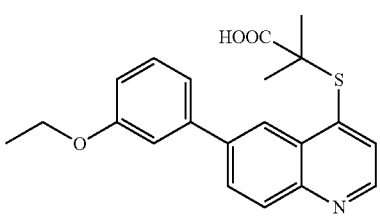
103 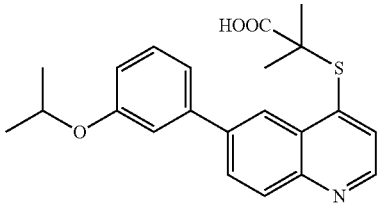
104 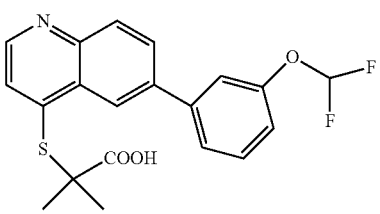
108 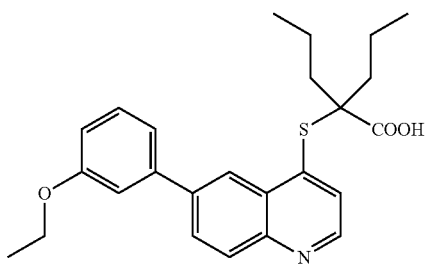
109 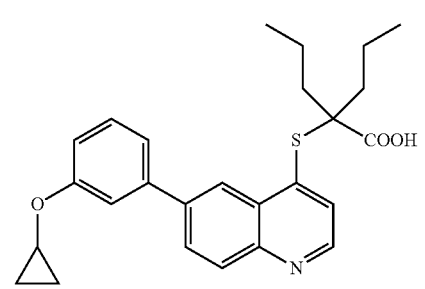
110 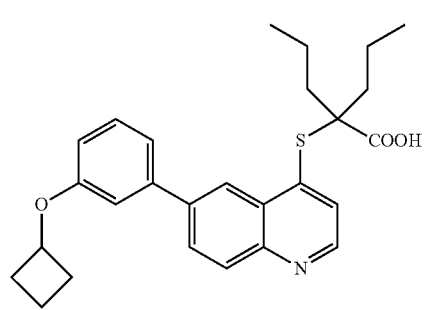

| | |
|---|---|
| 111 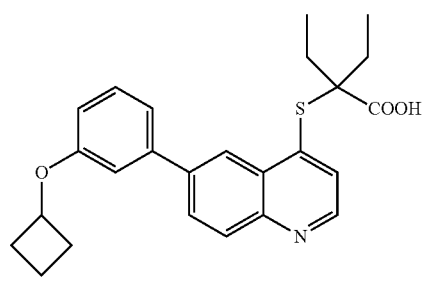 | 117 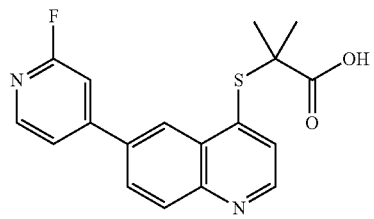 |
| 112 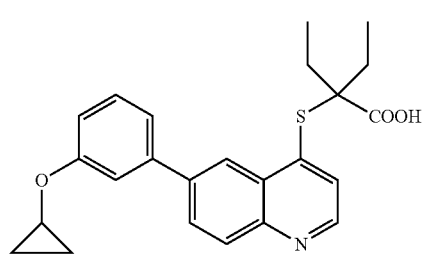 | 119 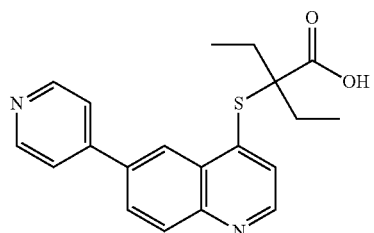 |
| 113 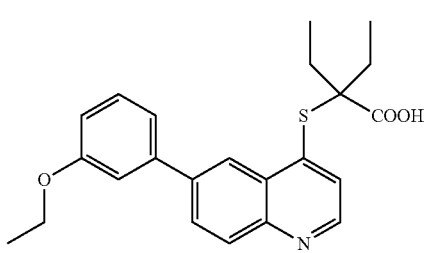 | 120 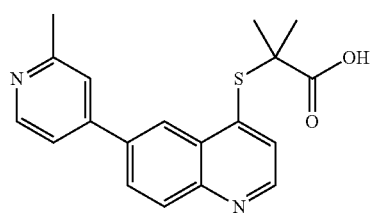 |
| 114 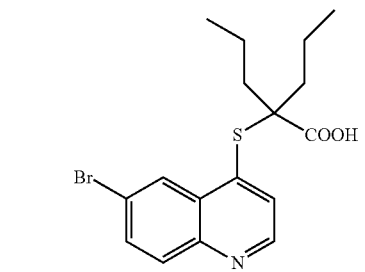 | 118 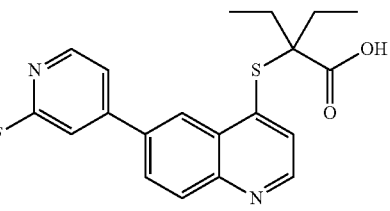 |
| 115 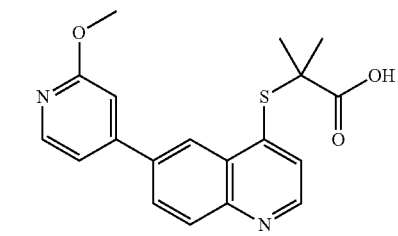 | 121 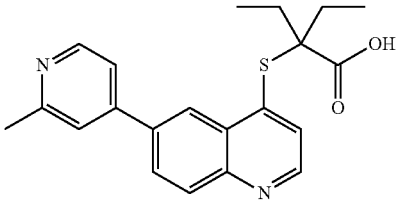 |
| 116 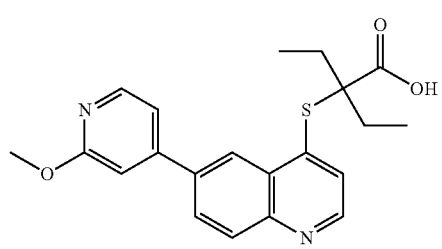 | 122 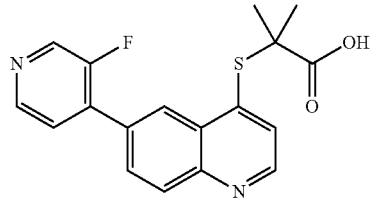 |
| | 123 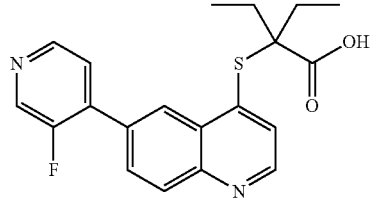 |

-continued

133 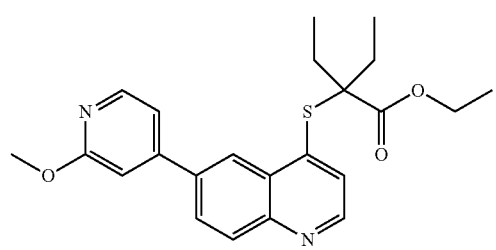
134 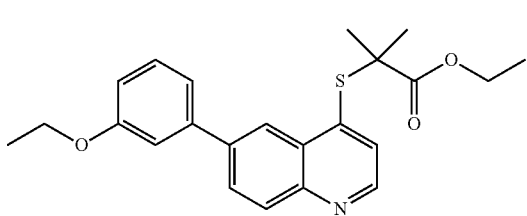
135 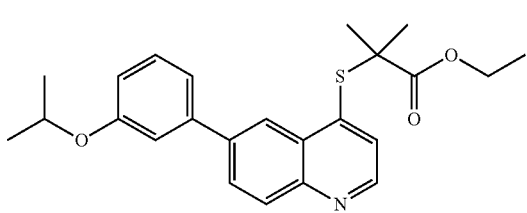
136 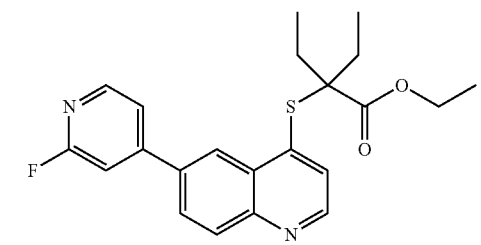
137 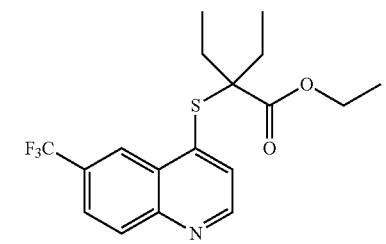
138 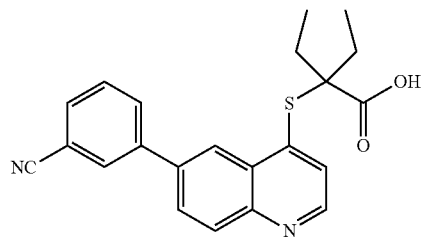
139 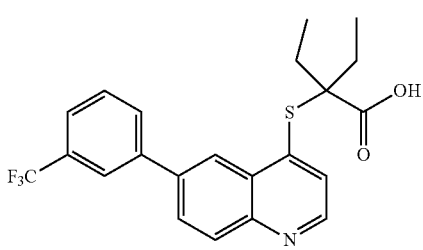
140 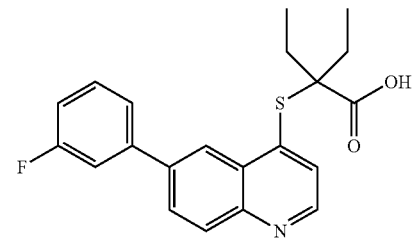
141 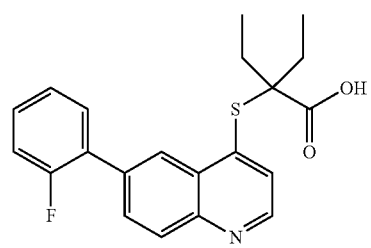
142 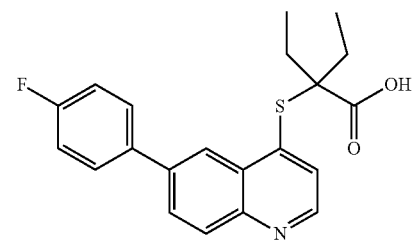
The present invention provides the method for preparation of said compounds, including the procedure carried out by the following route,
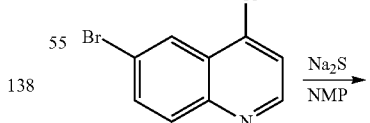
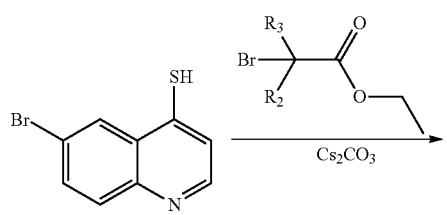

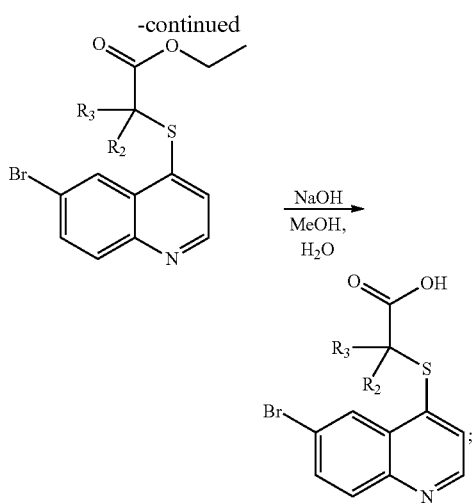

or including the procedure carried out by the following route,

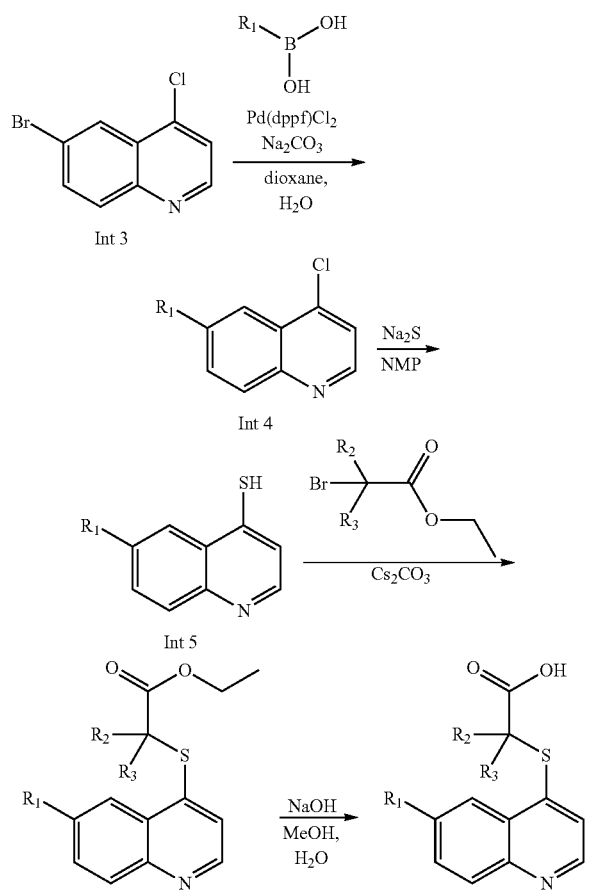

The present invention provides the use of said compounds or optical isomers or solvates or pharmaceutically acceptable salts or pro-drugs thereof in the preparation of URAT1 inhibitory drugs. Further, the drugs are applied in the prevention and/or treatment of gout, recurrent gout attack, gouty arthritis, hyperuricemia, hypertension, cardiovascular diseases, coronary artery disease, Lesch-Nyhan syndrome, Kearns-Sayre Syndrome, nephropathy, kidney stone, renal failure, joint inflammation, arthritis, urolithiasis, lead poisoning, hyperparathyroidism, psoriasis, sarcoidosis or hypoxanthine-guanine phosphoribosyl transferase deficiency disease, and the drugs for prevention and/or treatment of gout or hyperuricemia are preferable.

The present invention also provides a combination, that is a formulation prepared with the compounds or optical isomers or solvates or pharmaceutically acceptable salts or pro-drugs thereof according to the claims, together with the pharmaceutically acceptable auxiliary materials.

The present invention also provides the use of the combination in the preparation of URAT1 inhibitory drugs.

Further, the drugs are applied in the prevention and/or treatment of gout, recurrent gout attack, gouty arthritis, hyperuricemia, hypertension, cardiovascular diseases, coronary artery disease, Lai-naphthalene syndrome, Kai-Sai syndrome, nephropathy, kidney stone, renal failure, joint inflammation, arthritis, urolithiasis, lead poisoning, hyperparathyroidism, psoriasis, sarcoidosis or hypoxanthine-guanine phosphoribosyl transferase deficiency disease, and the drugs for prevention and/or treatment of gout or hyperuricemia are preferable.

Various compounds and salts, hydrates or optical isomers or solvates or pharmaceutically acceptable salts or pro-drugs thereof provided in the present invention are a kind of selective uric acid reabsorption inhibitors, which can be used in the treatment of hyperuricemia and gout by promoting uric acid to excrete from the body and reducing serum uric acid, and have the effect of reducing the uric acid in the animal body and human body.

In addition, for the compounds of the present invention, their isotopic substituents, such as deuteration, tritium, $^{14}C$ and $^{15}N$ substituted ones, also have the same activities and applications. For example, the isotopically substituents can be obtained by replacing hydrogen with deuterium and/or tritium. Similarly, naturally abundant $^{12}C$ can be replaced by $^{13}C$ or $^{14}C$, naturally abundant $^{14}N$ by $^{15}N$, and naturally abundant $^{16}O$ by $^{17}O$ or $^{18}O$ and the same or any combination.

In the present invention, said $C_1$-$C_6$ alkyl denotes $C_1$, $C_2$, $C_3$, $C_4$, $C_5$, and $C_6$ alkyls, i.e. straight or branched alkyl with 1-6 carbon atoms, such as methyl, ethyl, propyl, butyl, pentyl, hexyl, isopropyl, isobutyl, t-butyl, sec-butyl, t-butylmethyl and the similar.

In the present invention, said $C_3$-$C_6$ cycloalkyl denotes $C_3$, $C_4$, $C_5$, and $C_6$ cyclic alkyl, containing 3-6 carbon atoms, such as cyclopropyl, cyclobutyl, cyclopentyl, cyclohexyl, cyclopropylmethyl, cyclobutylmethyl, cyclopentylmethyl and so on.

In the present invention, "pharmaceutically acceptable" denotes that chemically or physically, certain carriers, vehicles, diluents, adjuvants and/or resultant salts are usually compatible with other components of a drug dosage form and are also physiologically compatible with the receptor.

In the present invention, "salts" refer to those acid and/or basic salts formed by the compounds or their stereoisomers with inorganic and/or organic acids or bases, and also include amphoteric ionic salts (inner salts), and further include quaternary ammonium salts, such as alkyl ammonium salts. These salts can be directly obtained from the final separation and purification of compounds, and also can be obtained by suitably mixing the compounds or their stereoisomers with certain amount of acid or base (such as equal equivalence). These salts maybe form precipitation in the solution and are collected by filtration, or are obtained after evaporation of solvent, or are prepared by freeze drying after reaction in aqueous medium. In the present invention, said salts may be hydrochlorate, sulfate, citrate, benzenesulphonate, hydrobromate, hydrofluoride, phosphate, acetate, propionate, succinate, oxalate, malate, succinate, fumarate, maleate, tartrate or trifluoroacetate of compounds, and also can be alkali metal ion salts such as sodium salt, potassium salt.

Obviously, based on above contents of the present invention, other various kinds of modification, alternation, or variation can be realized according to ordinary technical knowledge and common means in the art, without departing from above basic technical ideas of the present invention.

Above contents of the present invention will be further elucidated in detail with reference to the specific embodiments of examples. However, it should not be construed that the above subject scope of the present invention is only limited to the following examples. All of the technologies realized based on the above contents of the present invention belong to the scope of the present invention.

EMBODIMENTS

The general reaction scheme was described as below:

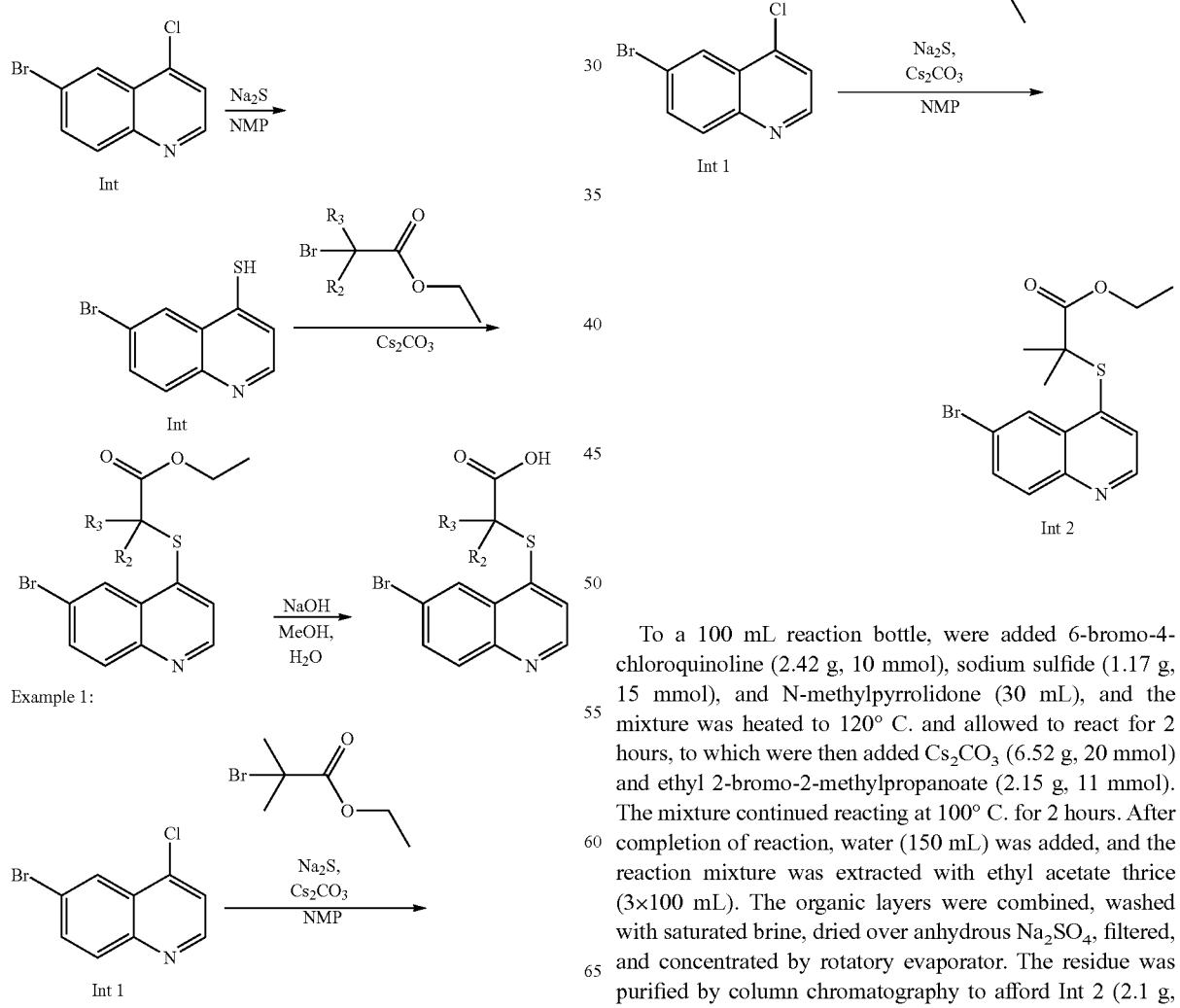

Example 1:

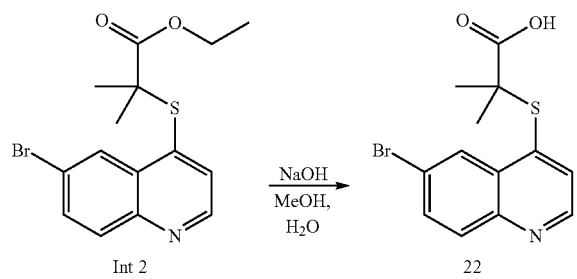

Synthesis of ethyl 2-((6-bromoquinolin-4-yl)thio)-2-methylpropanoate (Int. 2)

To a 100 mL reaction bottle, were added 6-bromo-4-chloroquinoline (2.42 g, 10 mmol), sodium sulfide (1.17 g, 15 mmol), and N-methylpyrrolidone (30 mL), and the mixture was heated to 120° C. and allowed to react for 2 hours, to which were then added Cs$_2$CO$_3$ (6.52 g, 20 mmol) and ethyl 2-bromo-2-methylpropanoate (2.15 g, 11 mmol). The mixture continued reacting at 100° C. for 2 hours. After completion of reaction, water (150 mL) was added, and the reaction mixture was extracted with ethyl acetate thrice (3×100 mL). The organic layers were combined, washed with saturated brine, dried over anhydrous Na$_2$SO$_4$, filtered, and concentrated by rotatory evaporator. The residue was purified by column chromatography to afford Int 2 (2.1 g, yield 60%), MS: 354, 356 (M+H$^+$).

Synthesis of 2-((6-bromoquinolin-4-yl)thio)-2-methylpropanoic Acid (22)

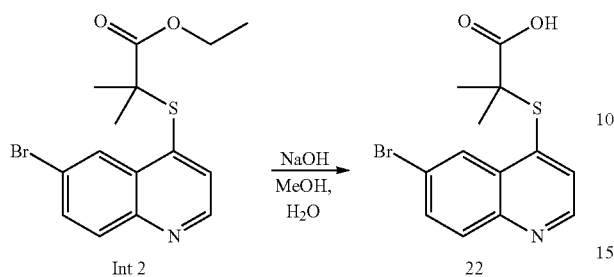

To a 100 mL reaction bottle, were added Int. 2 (354 mg, 1 mmol), CH$_3$OH (5 mL), and water (5 mL), and the mixture was allowed to react at room temperature for 16 hours. After completion of reaction, the mixture was adjusted to about pH 5 with 2N HCl in icewater bath, then filtered. The filter cake was washed with water (10 mL), and dried to provide compound 22 (228 mg, yield 70%). $^1$H NMR (400 MHz, DMSO): δ (ppm) 13.09 (s, 1H), 8.89 (d, J=4.0 Hz, 1H), 8.51 (d, J=4.0 Hz, 1H), 7.96 (m, 2H), 7.64 (d, J=4.0 Hz, 1H), 1.55 (s, 6H). MS: 326.1, 328.1 (M+H$^+$).

The target products 23, 24, 83, 93, 94, 95, 96, 114, 128, 129 were synthesized according to the same method, using the corresponding reagents.

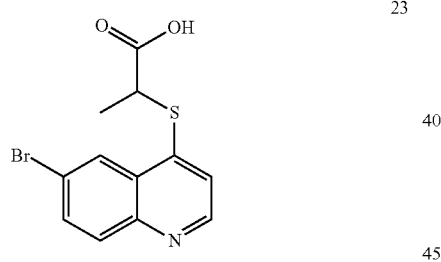

Product 23 (2-(6-bromoquinolin-4-ylthio)propanoic acid): 312.0, 314.0 (M+H$^+$).

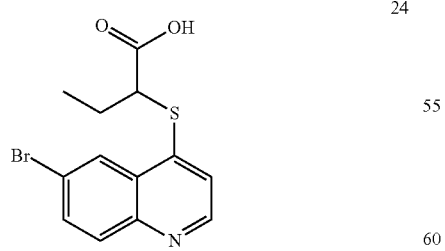

Product 24 (2-(6-bromoquinolin-4-ylthio)butanoic acid): $^1$H NMR (DMSO, 400 MHz): δ (ppm) 13.22 (s, 1H), 8.81 (d, J=4.8 Hz, 1H), 8.28 (d, J=1.2 Hz, 1H), 7.99-7.94 (m, 2H), 7.65 (d, J=4.8 Hz, 1H), 4.29 (t, J=7.2 Hz, 1H), 2.01-1.90 (m, 2H), 1.06 (t, J=7.2 Hz, 3H); MS: 325.9, 327.9 (M+H$^+$).

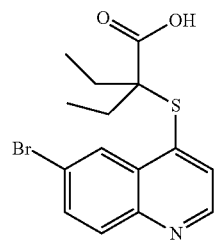

Product 83 (2-(6-bromoquinolin-4-ylthio)-2-ethylbutanoic acid): $^1$H NMR (DMSO, 400 MHz): δ (ppm) 13.09 (s, 1H), 8.87 (d, J=4.0 Hz, 1H), 8.56 (d, J=4.0 Hz, 1H), 7.96 (m, 2H), 7.61 (d, J=4.0 Hz, 1H), 1.84-1.77 (m, 4H), 0.92 (t, 6H). MS: 354.0, 356.0 (M+H$^+$).

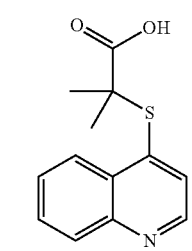

Product 93 (2-(quinolin-4-ylthio)-2-methylpropanoic acid): $^1$H NMR (CDCl$_3$, 400 MHz): δ (ppm) 8.60 (d, J=4.0 Hz, 1H), 8.35 (d, J=4.0 Hz, 1H), 8.07 (d, J=4.0 Hz, 1H), 7.65 (m, 2H), 7.51 (t, J=4.0 Hz, 1H), 1.81 (t, 6H). MS: 324.1 (M+H$^+$).

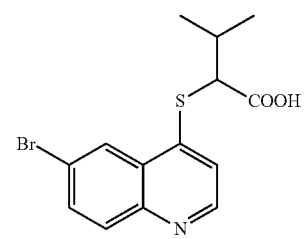

Product 94 (2-(6-bromoquinolin-4-ylthio)-3-methylbutanoic acid): $^1$H NMR (DMSO, 400 MHz): δ (ppm) 13.10 (s, 1H), 8.79 (d, J=8.0 Hz, 1H), 8.29 (d, J=4.0 Hz, 1H), 7.96 (m, 2H), 7.61 (d, J=8.0 Hz, 1H), 4.13 (d, J=7.6 Hz, 1H), 2.27-2.24 (m, 1H), 1.14-1.10 (t, 6H). MS: 340.0, 342.0 (M+H$^+$).

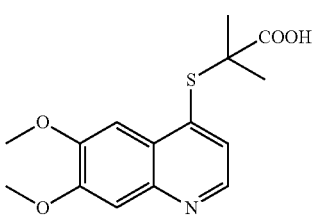

Product 95 (2-(6,7-dimethoxyquinolin-4-ylthio)-2-methylpropanoic acid): ¹H NMR (DMSO, 400 MHz): δ (ppm) 8.62 (d, J=4.0 Hz, 1H), 7.67 (s, 1H), 7.45 (d, J=4.0 Hz, 1H), 7.40 (1H, s), 3.94 (6H, s), 1.51 (6H, s); MS: 308.1 (M+H⁺).

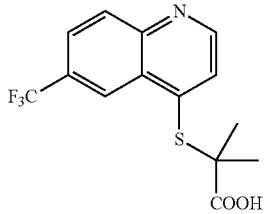

96

Product 96 (2-(6-trifluoromethylquinolin-4-ylthio)-2-methylpropanoic acid): ¹H NMR (DMSO, 400 MHz): δ (ppm) 13.10 (s, 1H), 8.96 (d, J=8.0 Hz, 1H), 8.28 (d, J=4.0 Hz, 1H), 8.05 (m, 2H), 7.40 (d, J=8.0 Hz, 1H), 1.5 (s, 6H); MS: 316.0 (M+H⁺).

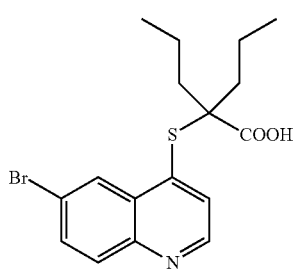

114

Product 114 (2-(6-bromoquinolin-4-ylthio)-2-propylpentanoic acid): ¹H NMR (DMSO, 400 MHz): δ (ppm): 8.84 (d, J=4.0 Hz, 1H), 8.54 (d, J=4.0 Hz, 1H), 7.94 (m, 2H), 7.61 (d, J=4.0 Hz, 1H), 1.78-1.65 (m, 4H), 1.46-1.29 (m, 4H), 0.89-0.82 (m, 6H); MS: 381.9, 383.9 (M+H⁺).

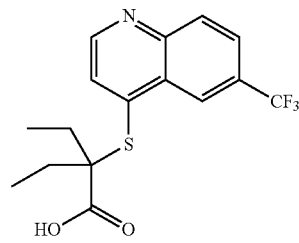

128

Product 128 (2-(6-trifluoromethyl-quinolin-4-ylthio)-2-propylpentanoic acid): ¹H NMR (DMSO, 400 MHz): δ (ppm): 13.01 (s, 1H), 8.81 (d, J=4.0 Hz, 1H), 8.47 (d, J=4.0 Hz, 1H), 7.94 (m, 2H), 7.59 (d, J=4.0 Hz, 1H), 1.77-1.62 (m, 4H), 1.45-1.27 (m, 4H), 0.87-0.80 (m, 6H); MS: 344.1 (M+H⁺).

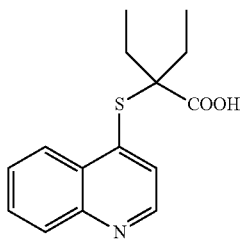

129

Product 129 (2-(quinolin-4-ylthio)-2-propylpentanoic acid) MS: 276.1 (M+H⁺)

Example 2

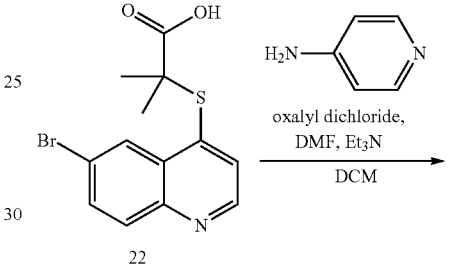

22

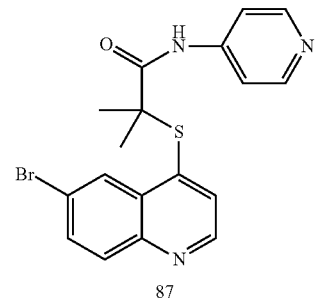

87

Synthesis of Product 87

To a 100 mL reaction bottle, were added Int. 2 (325 mg, 1 mmol), dichloromethane (10 mL), DMF (20 mg), and then oxalyl chloride (1 g, 8 mmol) was added. The mixture was heated to 40° C. and allowed to react for 1 hour, and concentrated to dry. Then, CH₂Cl₂ (10 mL) and triethylamine (500 mg, 5 mmol) were added, and 4-aminopyridine (190 mg, 2 mmol) was finally added. The mixture was heated to 40° C. and reacted for 1 hour. After completion of reaction, water (50 mL) was added, and the mixture was extracted with ethyl acetate (3×50 mL) thrice. The organic layers were combined, washed with saturated brine, dried over anhydrous Na₂SO₄, filtered, and concentrated by rotatory evaporator. The residue was purified by column chromatography to afford the product 87 (160 mg, yield 40%). MS: 401.0, 403.0 (M+H⁺).

The target products 88, 89, 90, 91, 92 were synthesized as the same method, using corresponding reagents.

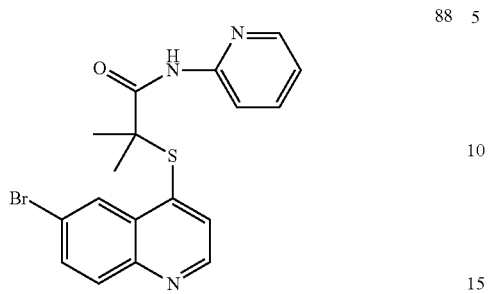

Product 88 (2-(6-bromoquinolin-4-ylthio)-2-methylpropionyl-(2-aminopyridine)): MS: 401.0, 403.0 (M+H$^+$).

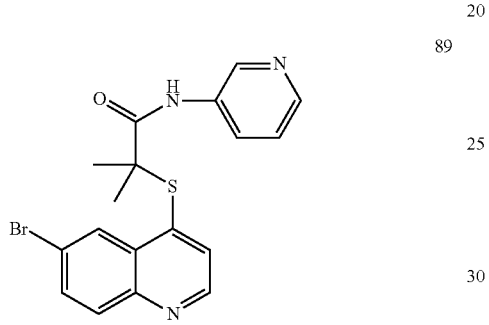

Product 89 (2-(6-bromoquinolin-4-ylthio)-2-methylpropionyl-(3-aminopyridine)): MS: 401.0, 403.0 (M+H$^+$).

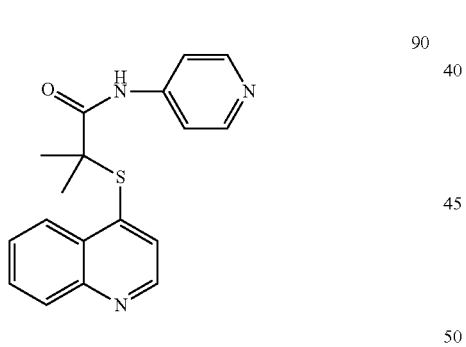

Product 90 (2-(quinolin-4-ylthio)-2-methylpropionyl-(4-aminopyridine)): MS: 324.1 (M+H$^+$).

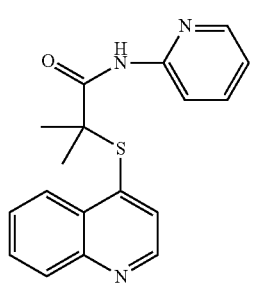

Product 91 (2-(quinolin-4-ylthio)-2-methylpropionyl-(2-aminopyridine)): MS: 324.1 (M+H$^+$).

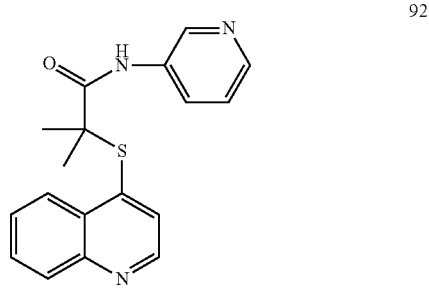 [SMILES: CC(C)(Sc1ccnc2ccccc12)C(=O)Nc1cccnc1]

Product 92 (2-(quinolin-4-ylthio)-2-methylpropionyl-(3-aminopyridine)): MS: 324.1 (M+H$^+$).

Example 3

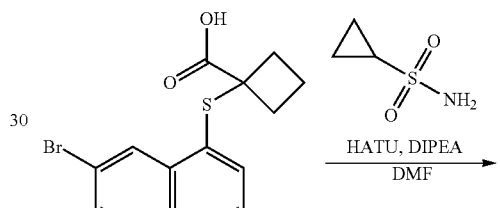

To a 50 mL reaction bottle, were added Int. A-1 (112 mg, 0.33 mmol), cyclopropanesulfonamide (52 mg, 0.43 mmol), HATU (163 mg, 0.43 mmol), DIPEA (129 mg, 1 mmol), and DMF (3 mL), and stirred at room temperature for 16 hours. After completion of reaction, water (20 mL) was added, and the mixture was extracted with ethyl acetate (15 mL×3) and dried by rotatory evaporator. The residue was purified by prep-HPLC to afford compound 105 (50 mg, yield 34%). $^1$H NMR (400 MHz, CDCl$_3$) δ 8.70 (d, J=4.6 Hz, 1H), 8.23 (d, J=2.0 Hz, 1H), 8.01 (d, J=8.8 Hz, 1H), 7.85 (m, 1H), 6.95 (d, J=4.8 Hz, 1H), 3.18-3.10 (m, 2H), 2.83-2.73 (m, 2H), 2.42 (dd, J=11.2 Hz, 2H), 2.26-2.14 (m, 1H), 1.18-1.12 (m, 2H), 0.91-0.84 (m, 2H). MS: 440.8, 442.8 (M+H$^+$).

Compounds 106 and 107 were prepared according to the same preparative way, using the corresponding starting materials.

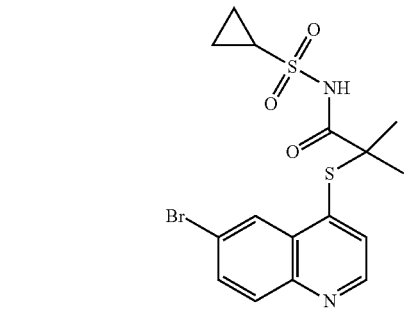

Product 106 2-(6-bromoquinolin-4-ylthio)-N-(cyclopropylsulfonyl)-2-methylpropanamide: $^1$H NMR (400 MHz, CDCl$_3$) δ 8.78 (d, J=4.7 Hz, 1H), 8.41 (d, J=2.1 Hz, 1H), 8.02 (d, J=8.9 Hz, 1H), 7.85 (m, 1H), 7.33 (d, J=4.6 Hz, 1H), 2.98-2.90 (m, 2H), 1.73 (s, 6H), 2.26-2.14 (m, 1H), 1.38-1.31 (m, 2H); MS: 428.8, 430.8 (M+H$^+$).

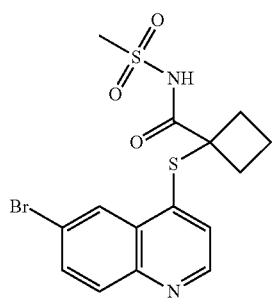

Product 107 1-(6-bromoquinolin-4-ylthio)-N-(methylsulfonyl)cyclobutyl-1-formamide (107): MS: 414.8, 416.8 (M+H$^+$).

Example 4

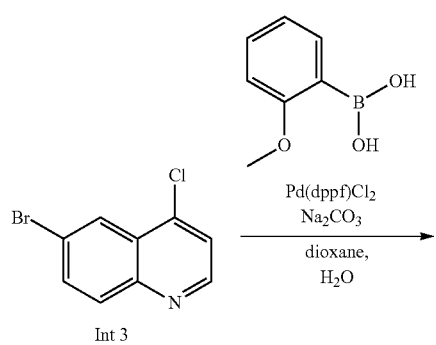

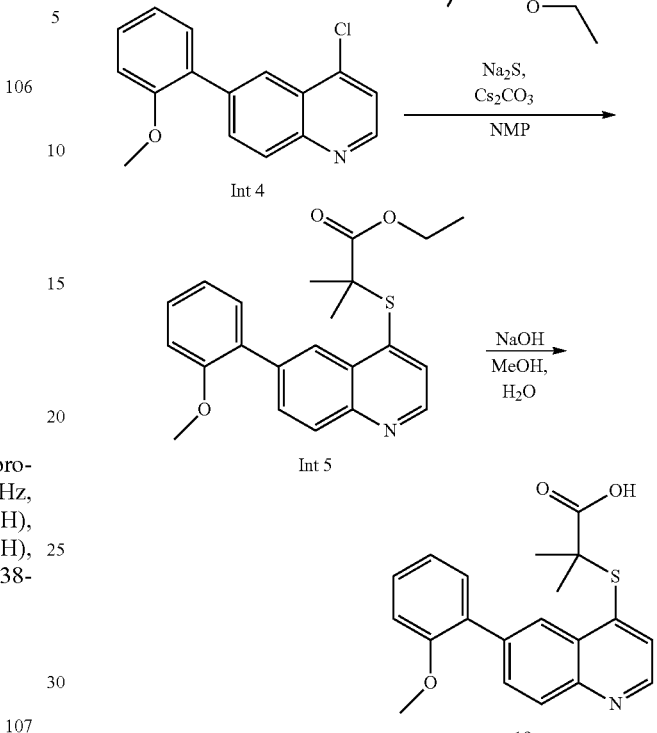

Synthesis of Int. 4

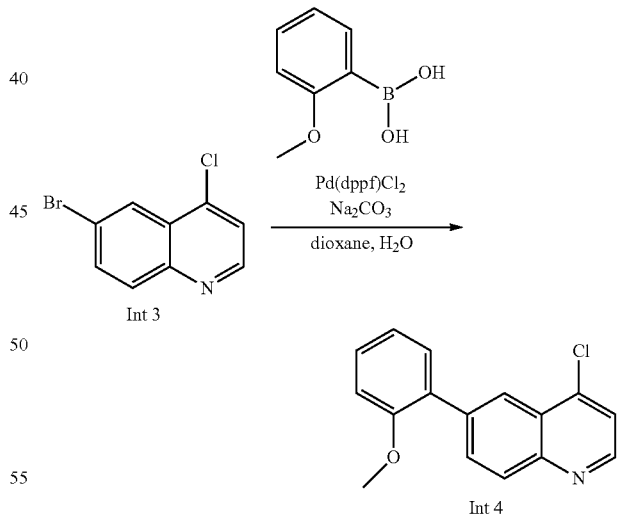

To a 50 mL reaction bottle, were added Int. 3 (241 mg, 1 mmol), 2-methoxyphenylboronic acid (152 mg, 1 mmol), Na$_2$CO$_3$ (212 mg, 2 mmol), Pd(dppf)Cl$_2$ (37 mg, 0.05 mmol), dioxane (6 mL), and water (3 mL), and then nitrogen was purged. The mixture was heated to 110° C. under protection of N$_2$ and allowed to react for 2 hours. After completion of reaction, water (50 mL) was added, and the mixture was extracted with ethyl acetate (3×50 ml) thrice. The organic layers were combined, washed with saturated brine, dried over anhydrous Na$_2$SO$_4$, filtered, and rotatory evaporated. The residue was purified by column chromatography to afford Int. 4 (190 mg, yield 50%). MS: 270.0, 272.0 (M+H$^+$).

Synthesis of Int. 5

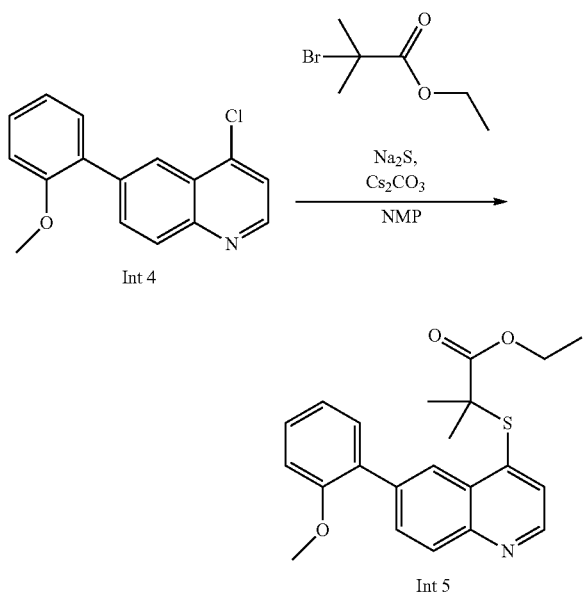

To a 100 mL reaction bottle, were added Int. 4 (2.69 g, 10 mmol), Na$_2$S (1.17 g, 15 mmol), N-methylpyrrolidone (30 mL), and the mixture was heated to 120° C. and allowed to react for 2 hours. Then, to the reaction bottle, were added Cs$_2$CO$_3$ (6.52 g, 20 mmol) and ethyl 2-bromo-2-methylpropanoate (2.15 g, 11 mmol), and the reaction mixture was continued being heated to 100° C. for 2 hours. After completion of reaction, 150 mL water was added, and the reaction mixture was extracted with ethyl acetate (3×100 ml) thrice. The organic layers were combined, washed with saturated brine, dried over anhydrous Na$_2$SO$_4$, filtered, and rotatory evaporated. The residue was purified by column chromatography to afford Int. 5 (2.1 g, yield 60%). MS: 382.0 (M+H$^+$).

Synthesis of 19

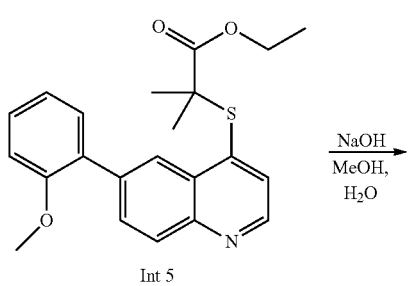

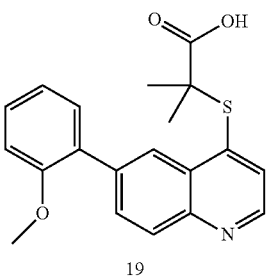

To a 100 mL reaction bottle, were added Int. 5 (381 mg, 1 mmol), CH$_3$OH (5 mL), and water (5 mL), and the mixture was allowed to react at room temperature for 16 hours. After completion of reaction, the reaction mixture was adjusted to about pH 5 with 2N HCl in icewater bath and filtered. The filter cake was washed with water (10 mL), and dried to provide compound 19 (247 mg, yield 70%). MS: 354.1 (M+H$^+$).

Compounds 1, 2, 3, 4, 5, 6, 7, 8, 9, 10, 11, 12, 13, 14, 15, 16, 17, 18, 20, 21, 25, 26, 27, 28, 29, 30, 31, 32, 33, 34, 35, 36, 37, 38, 39, 40, 41, 42, 84, 85, 86, 100, 101, 102, 103, 104, 108, 109, 110, 111, 112, 113, 115, 116, 117, 118, 119, 120, 121, 122, 123, 124, 125, 126, 127, 138, 139, 140, 141, 142 were synthesized according to the same method, using the corresponding reagents.

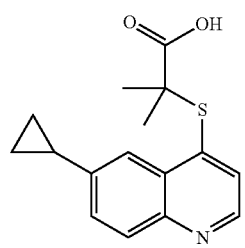

Product 1 (2-(6-cyclopropylquinolin-4-ylthio)-2-methylpropanoic acid: $^1$H NMR (400 MHz, DMSO): δ (ppm) 12.97 (s, 1H), 8.72 (d, J=4.0 Hz, 1H), 8.03 (d, J=4.0 Hz, 1H), 7.93 (d, J=4.0 Hz, 1H), 7.52-7.47 (m, 2H), 2.20-2.09 (m, 1H), 1.55 (s, 6H), 1.10-1.02 (m, 2H), 0.83-0.75 (m, 2H). MS: 288.1 (M+H$^+$).

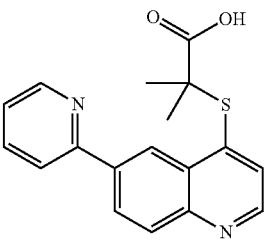

Product 2 (2-(6-(pyridin-2-yl)quinolin-4-ylthio)-2-methylpropanoic acid): MS: 325.1 (M+H$^+$).

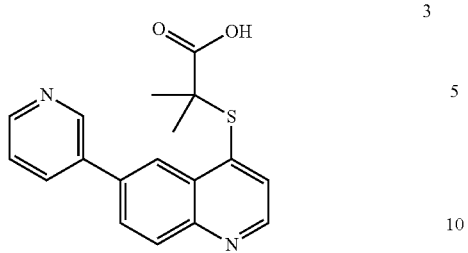

3

Product 3 (2-(6-(pyridin-3-yl)quinolin-4-ylthio)-2-methylpropanoic acid): $^1$H NMR (400 MHz, DMSO): δ (ppm) 12.94 (s, 1H), 9.04 (d, J=4.0 Hz, 1H), 8.88 (m, 1H), 8.66-8.62 (m, 2H), 8.22-8.16 (m, 3H), 7.66 (d, J=4.0 Hz, 1H), 7.58 (m, 1H), 1.58 (s, 6H). MS: 325.1 (M+H$^+$).

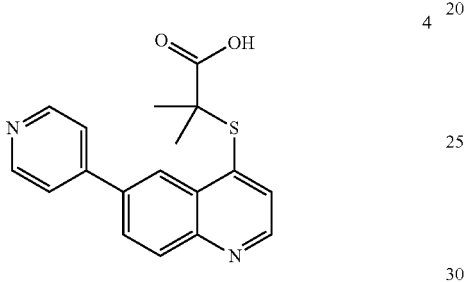

4

Product 4 (2-(6-(pyridin-4-yl)quinolin-4-ylthio)-2-methylpropanoic acid): $^1$H NMR (400 MHz, DMSO): δ (ppm) 13.00 (s, 1H), 8.90 (d, J=4.0 Hz, 1H), 8.74-8.70 (m, 3H), 8.22-8.20 (m, 2H), 7.86 (m, 2H), 7.67 (d, J=4.0 Hz, 1H), 1.58 (s, 6H). MS: 325.1 (M+H$^+$).

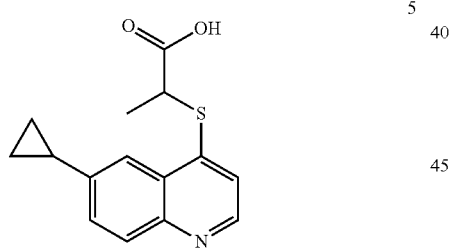

5

Product 5 (2-(6-cyclopropylquinolin-4-ylthio)propanoic acid: MS: 274.1 (M+H$^+$).

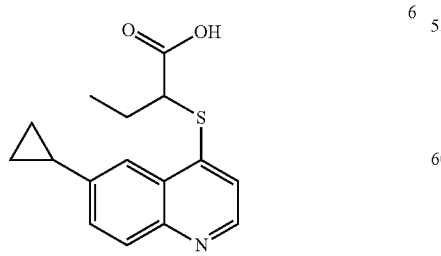

6

Product 6 (2-(6-cyclopropylquinolin-4-ylthio)butanoic acid): MS: 288.1 (M+H$^+$).

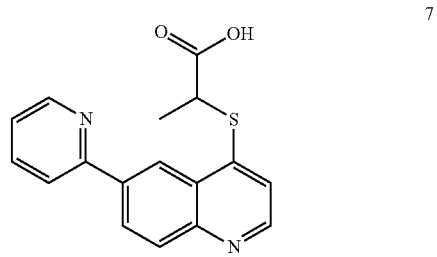 [SMILES: CC(Sc1ccnc2ccc(-c3ccccn3)cc12)C(=O)O]

7

Product 7 (2-(6-(pyridin-2-yl)quinolin-4-ylthio)propanoic acid): MS: 311.1 (M+H$^+$).

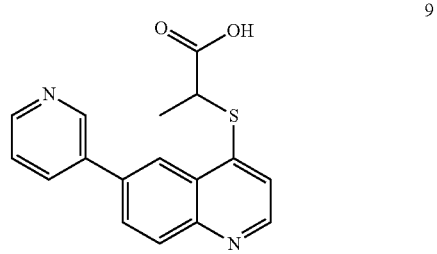 [SMILES: CC(Sc1ccnc2ccc(-c3cccnc3)cc12)C(=O)O]

8

Product 8 (2-(6-(pyridin-2-yl)quinolin-4-ylthio)butanoic acid): MS: 325.1 (M+H$^+$).

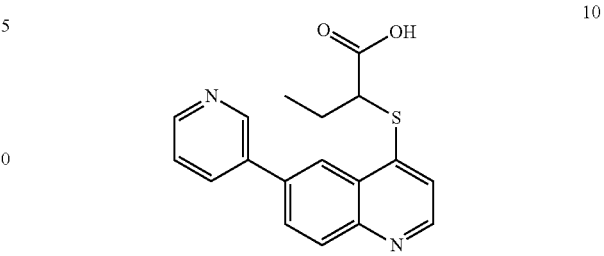

9

Product 9 (2-(6-(pyridin-3-yl)quinolin-4-ylthio)propanoic acid): MS: 311.1 (M+H$^+$).

10

Product 10 (2-(6-(pyridin-3-yl)quinolin-4-ylthio)butanoic acid): MS: 325.1 (M+H$^+$).

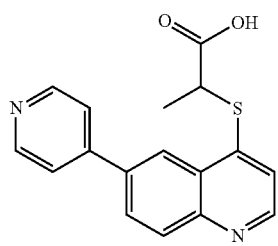

Product 11 2-((6-(pyridin-4-yl)quinolin-4-ylthio)propanoic acid): MS: 311.1 (M+H$^+$).

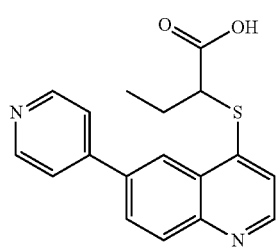

Product 12 (2-(6-(pyridin-4-yl)quinolin-4-ylthio)butanoic acid): MS: 325.1 (M+H$^+$).

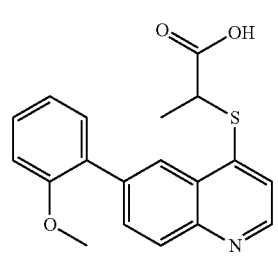

Product 13 (2-(6-(2-methoxyphenyl)-quinolin-4-ylthio)propanoic acid): MS: 340.1 (M+H$^+$).

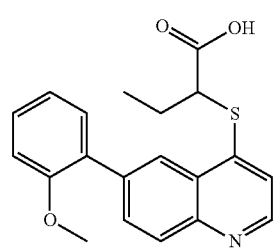

Product 14 (2-(6-(2-methoxyphenyl)quinolin-4-ylthio)butanoic acid): MS: 354.1 (M+H$^+$).

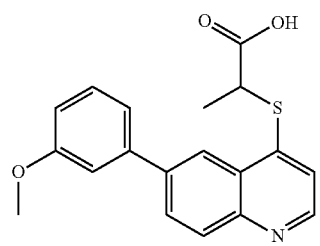

Product 15 (2-(6-(3-methoxyphenyl)-quinolin-4-ylthio) propanoic acid): MS: 340.1 (M+H$^+$).

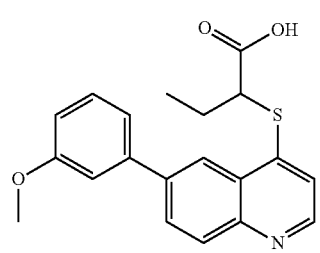

Product 16 (2-(6-(3-methoxyphenyl)-quinolin-4-ylthio) butanoic acid): MS: 354.1 (M+H$^+$).

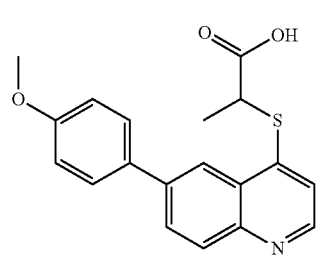

Product 17 (2-(6-(4-methoxyphenyl)-quinolin-4-ylthio) propanoic acid): MS: 340.1 (M+H$^+$).

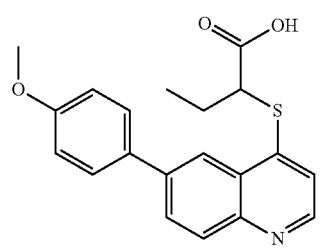

Product 18 (2-(6-(4-methoxyphenyl)quinolin-4-ylthio) butanoic acid): MS: 354.1 (M+H$^+$).

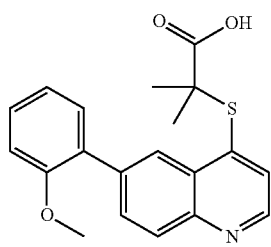

Product 19 (2-(6-(2-methoxyphenyl)-quinolin-4-ylthio)-2-methylpropanoic acid): $^1$H NMR (DMSO, 400 MHz): δ (ppm) 12.98 (s, 1H), 8.84 (d, J=4.0 Hz, 1H), 8.43 (d, J=4.0 Hz, 1H), 8.06 (d, J=4.0 Hz, 1H), 7.95 (m, 1H), 7.58 (d, J=4.0 Hz, 1H), 7.44-7.41 (m, 2H), 7.19 (d, J=4.0 Hz, 1H), 7.13-7.09 (m, 1H), 3.87 (s, 3H), 1.56 (s, 6H); MS: 354.1 (M+H$^+$).

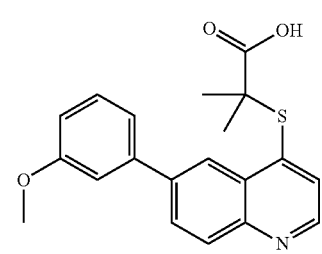

Product 20 (2-(6-(3-methoxyphenyl)-quinolin-4-ylthio)-2-methylpropanoic acid): $^1$H NMR (DMSO, 400 MHz): δ (ppm) 8.92 (d, J=4.9 Hz, 1H), 8.55 (d, J=1.8 Hz, 1H), 8.22 (dt, J=22.3, 5.3 Hz, 2H), 7.67 (d, J=4.9 Hz, 1H), 7.49 (t, J=7.9 Hz, 1H), 7.42-7.31 (m, 2H), 7.05 (dd, J=8.1, 1.8 Hz, 1H), 3.87 (s, 3H), 1.64 (s, 6H); MS: 354.1 (M+H$^+$).

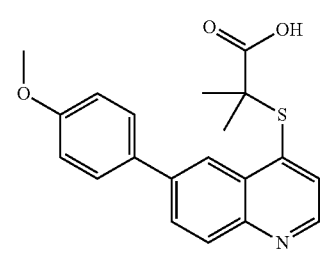

Product 21 (2-(6-(4-methoxyphenyl)quinolin-4-ylthio)-2-methylpropanoic acid): $^1$H NMR (DMSO, 400 MHz): δ (ppm) 12.99 (s, 1H), 8.81 (d, J=4.0 Hz, 1H), 8.51 (d, J=4.0 Hz, 1H), 8.10 (m, 2H), 7.77 (d, J=4.0 Hz, 2H), 7.60 (d, J=4.0 Hz, 1H), 7.11 (d, J=4.0 Hz, 2H), 3.84 (s, 3H), 1.57 (s, 6H); MS: 354.1 (M+H$^+$).

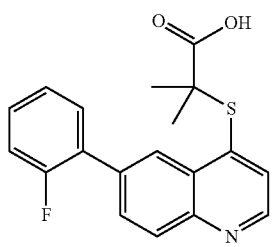

Product 25 (2-(6-(2-fluorophenyl)-quinolin-4-ylthio)-2-methylpropanoic acid): $^1$H NMR (DMSO, 400 MHz): δ (ppm) 13.02 (s, 1H), 8.88 (d, J=4.0 Hz, 1H), 8.52 (d, J=4.0 Hz, 1H), 8.15 (d, J=8.0 Hz, 1H), 8.02-8.0 (m, 1H), 8.00-7.99 (m, 1H), 7.72 (d, J=8.0 Hz, 1H), 7.54-7.49 (m, 1H), 7.43-7.38 (m, 2H), 1.57 (s, 6H); MS: 342.0 (M+H$^+$).

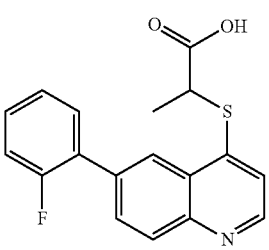

Product 26 (2-(6-(2-fluorophenyl)-quinolin-4-ylthio)propanoic acid): MS: 328.0 (M+H$^+$).

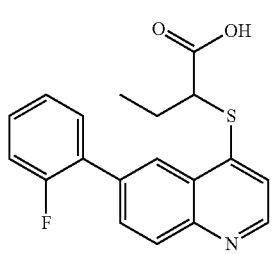

Product 27 (2-(6-(2-fluorophenyl)-quinolin-4-ylthio)butanoic acid): MS: 342.0 (M+H$^+$).

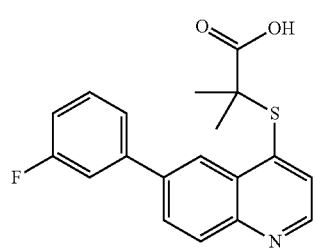

Product 28 (2-(6-(3-fluorophenyl)-quinolin-4-ylthio)-2-methylpropanoic acid): $^1$H NMR (DMSO, 400 MHz): δ (ppm) 12.97 (s, 1H), 8.87 (d, J=8.0 Hz, 1H), 8.59 (s, 1H), 8.18-8.13 (m, 2H), 7.69-7.60 (m, 4H), 7.32-7.27 (m, 1H), 1.58 (s, 6H); MS: 342.0 (M+H$^+$).

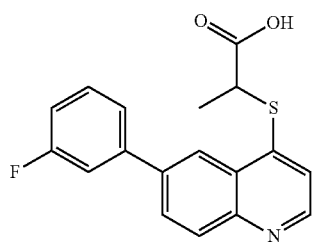

Product 29 (2-(6-(3-fluorophenyl)quinolin-4-ylthio)propanoic acid): MS: 328.0 (M+H⁺).

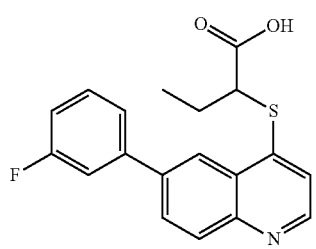

Product 30 (2-(6-(3-fluorophenyl)-quinolin-4-ylthio)butanoic acid): MS: 342.0 (M+H⁺).

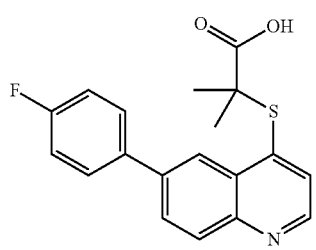

Product 31 (2-(6-(4-fluorophenyl)-quinolin-4-ylthio)-2-methylpropanoic acid): MS: 342.0 (M+H⁺).

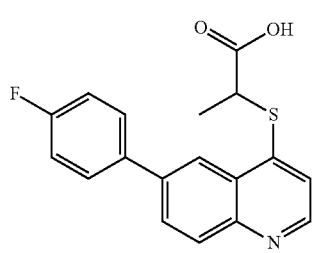

Product 32 (2-(6-(4-fluorophenyl)quinolin-4-ylthio)propanoic acid): MS: 328.0 (M+H⁺).

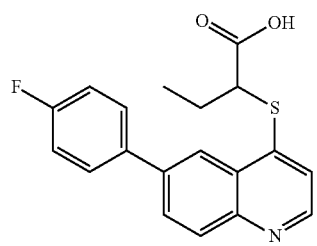

Product 33 (2-(6-(4-fluoro-phenyl)-quinolin-4-ylthio)butanoic acid): MS: 342.0 (M+H⁺).

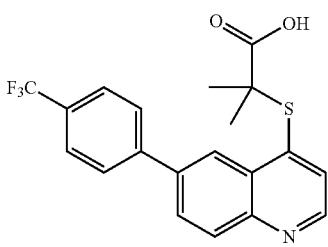

Product 34 (2-(6-(4-(trifluoromethyl)phenyl)quinolin-4-ylthio)-2-methylpropanoic acid): ¹H NMR (DMSO, 400 MHz): δ (ppm) 12.98 (s, 1H), 8.89 (d, J=4.0 Hz, 1H), 8.64 (s, 1H), 8.19 (d, J=4.0 Hz, 2H), 8.06 (d, J=4.0 Hz, 2H), 7.91 (d, J=4.0 Hz, 2H), 7.66 (d, J=4.0 Hz, 1H), 1.57 (s, 6H); MS: 392.0 (M+H⁺).

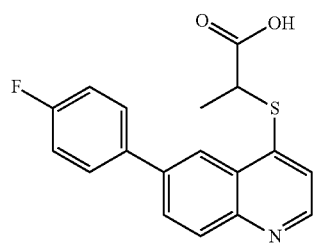

Product 35 (2-(6-(4-trifluoromethyl-phenyl)-quinolin-4-ylthio)propanoic acid): MS: 378.0 (M+H⁺).

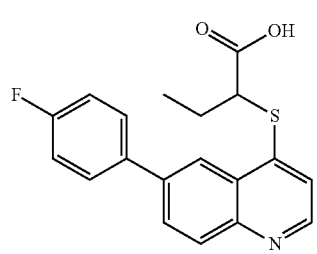

Product 36 (2-(6-(4-trifluoromethyl-phenyl)-quinolin-4-ylthio)butanoic acid): MS: 392.0 (M+H⁺).

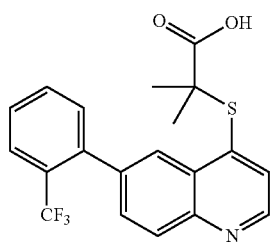

Product 37 (2-(6-(2-(trifluoromethyl-phenyl)-quinolin-4-ylthio)-2-methylpropanoic acid): ¹H NMR (DMSO, 400 MHz): δ (ppm) 13.02 (s, 1H), 8.89 (d, J=4.0 Hz, 1H), 8.25 (d, J=4.0 Hz, 1H), 8.12 (d, J=8.0 Hz, 1H), 7.91 (d, J=4.0 Hz, 1H), 7.78-7.70 (m, 3H), 7.61-7.55 (m, 2H), 1.53 (s, 6H); MS: 392.0 (M+H⁺).

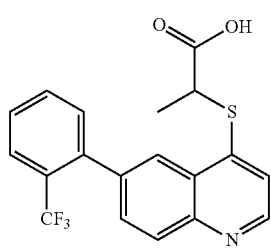

Product 38 (2-(6-(2-trifluoromethyl-phenyl)-quinolin-4-ylthio)propanoic acid): MS: 378.0 (M+H⁺).

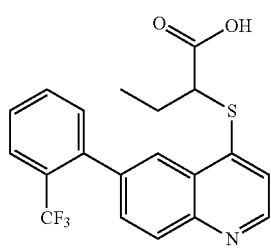

Product 39 (2-(6-(2-trifluoromethyl-phenyl)-quinolin-4-ylthio)butanoic acid): MS: 392.0 (M+H⁺).

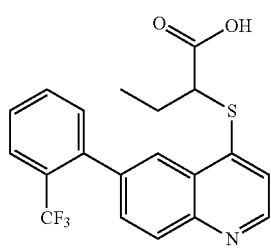

Product 40 (2-(6-(3-trifluoromethyl-phenyl)quinolin-4-ylthio)-2-methylpropanoic acid): MS: 392.0 (M+H⁺).

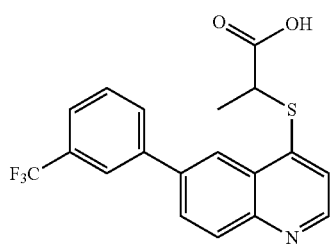

Product 41 (2-(6-(3-trifluoromethyl-phenyl)-quinolin-4-ylthio)propanoic acid): MS: 378.0 (M+H⁺).

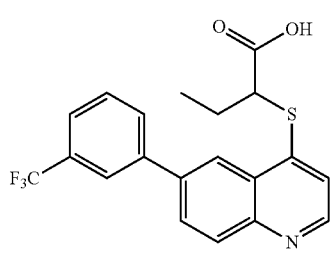

Product 42 (2-(6-(3-trifluoromethyl-phenyl)-quinolin-4-ylthio)butanoic acid): MS: 392.0 (M+H⁺).

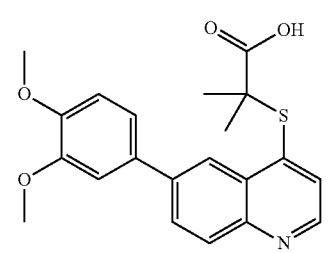

Product 84 (2-(6-(3,4-dimethoxy-phenyl)-quinolin-4-yl-thio)-2-methylpropanoic acid): MS: 384.0 (M+H⁺).

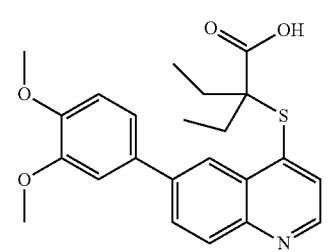

Product 85 (2-(6-(3,4-dimethoxy-phenyl)-quinolin-4-yl-thio)-2-ethylbutanoic acid): MS: 412.0 (M+H⁺).

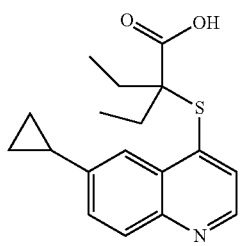

Product 86 (2-(6-cyclopropylquinolin-4-ylthio)-2-ethylbutanoic acid): MS: 316.0 (M+H$^+$).

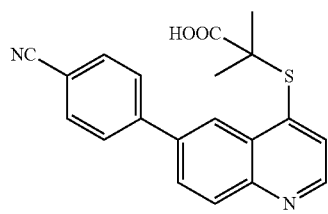

Product 100 (2-(6-(4-cyano-phenyl)-quinolin-4-ylthio)-2-methylpropanoic acid): MS: 349.0 (M+H$^+$).

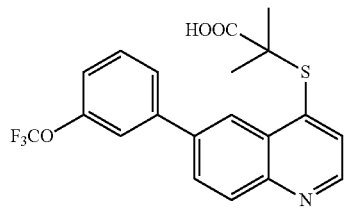

Product 101 (2-(6-(3-trifluoromethoxy-phenyl)-quinolin-4-ylthio)-2-methylpropanoic acid (101): MS: 408.0 (M+H$^+$).

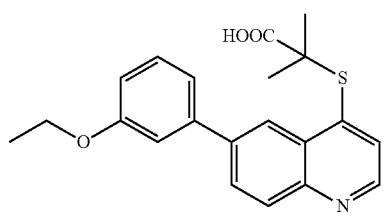

Product 102 (2-(6-(3-ethoxy-phenyl)-quinolin-4-ylthio)-2-methylpropanoic acid): MS: 368.0 (M+H$^+$).

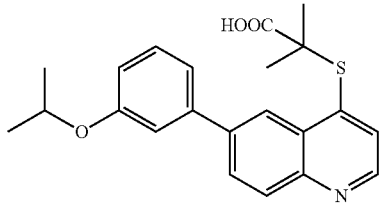

Product 103 (2-(6-(3-isopropoxy-phenyl)-quinolin-4-ylthio)-2-methylpropanoic acid): MS: 382.0 (M+H$^+$).

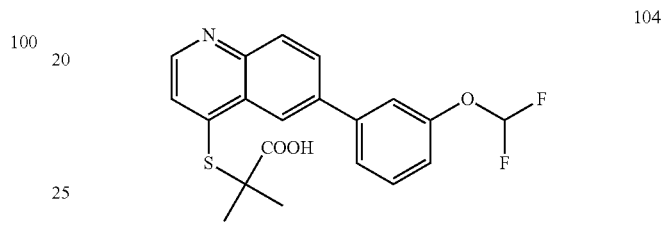

Product 104 (2-(6-(3-(difluoromethoxy-phenyl)-quinolin-4-ylthio)-2-methylpropanoic acid): MS: 390.0 (M+H$^+$).

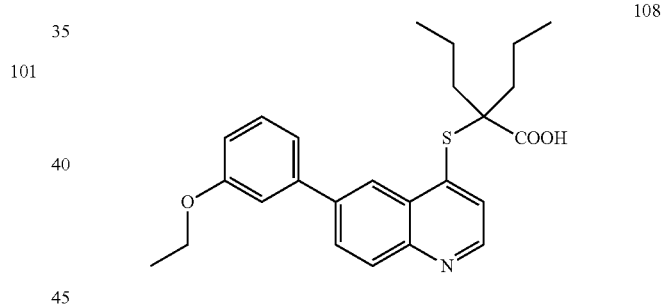

Product 108 (2-(6-(3-ethoxy-phenyl)-quinolin-4-ylthio)-2-propylpentanoic acid): MS: 424.1 (M+H$^+$).

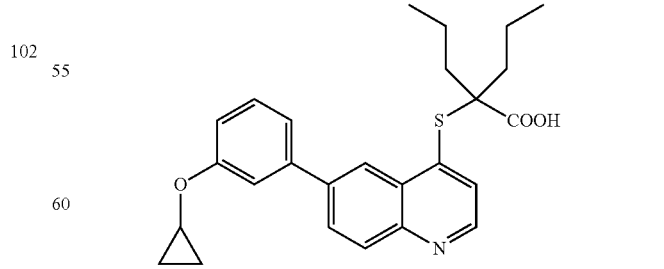

Product 109 (2-(6-(3-cyclopropyloxy-phenyl)-quinolin-4-ylthio)-2-propylpentanoic acid): MS: 436.1 (M+H$^+$).

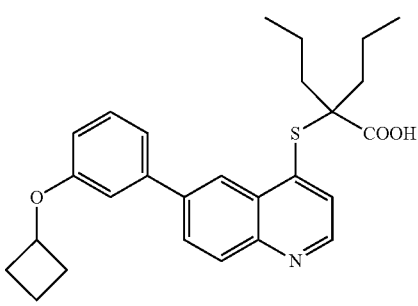

Product 110 (2-(6-(3-cyclobutyloxy-phenyl)-quinolin-4-ylthio)-2-propylpentanoic acid): MS: 450.1 (M+H$^+$).

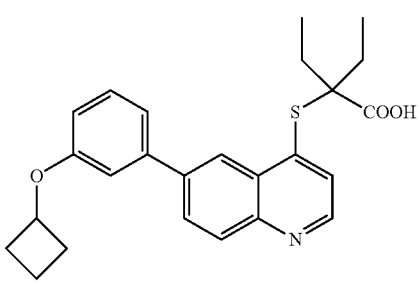

Product 111 (2-(6-(3-cyclobutyloxy-phenyl)-quinolin-4-ylthio)-2-ethylbutanoic acid): MS: 422.1 (M+H$^+$).

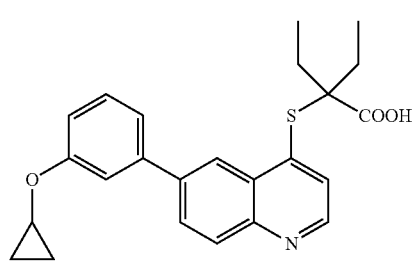

Product 112 (2-(6-(3-cyclopropyloxy-phenyl)-quinolin-4-ylthio)-2-ethylbutanoic acid): MS: 408.1 (M+H$^+$).

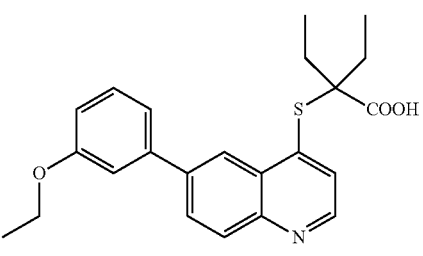

Product 113 (2-(6-(3-ethoxy-phenyl)-quinolin-4-ylthio)-2-ethylbutanoic acid): MS: 396.1 (M+H$^+$).

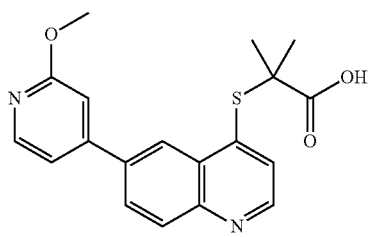

Product 115 (2-(6-(2-methoxypyridin-4-yl)quinolin-4-ylthio)-2-methylpropanoic acid): $^1$H NMR (DMSO, 400 MHz): δ (ppm): 13.02 (s, 1H), 8.95 (d, J=4.0 Hz, 1H), 8.77 (d, J=4.0 Hz, 1H), 8.36 (d, J=4.0 Hz, 1H), 8.20 (m, 2H), 7.66 (d, J=4.0 Hz, 1H), 7.47 (m, 1H), 7.24 (s, 1H), 3.94 (s, 3H), 0.95-0.85 (m, 6H); MS: 355.1 (M+H$^+$).

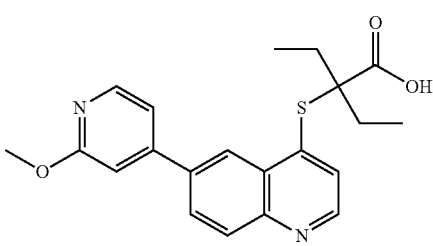

Product 116 (2-(6-(2-methoxypyridin-4-yl)quinolin-4-ylthio)-2-ethylbutanoic acid): $^1$H NMR (DMSO, 400 MHz): δ (ppm): 12.96 (s, 1H), 8.87 (d, J=4.0 Hz, 1H), 8.74 (d, J=4.0 Hz, 1H), 8.33 (d, J=4.0 Hz, 1H), 8.18 (m, 2H), 7.64 (d, J=4.0 Hz, 1H), 7.44 (m, 1H), 7.24 (s, 1H), 3.94 (s, 3H), 1.91-1.82 (m, 4H), 0.95-0.85 (m, 6H); MS: 383.2 (M+H$^+$).

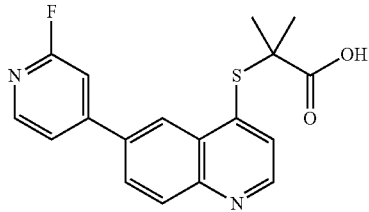

Product 117 (2-(6-(2-fluoropyridin-4-yl)-quinolin-4-ylthio)-2-methylpropanoic acid): $^1$H NMR (DMSO, 400 MHz): δ (ppm): 13.02 (s, 1H), 8.95 (d, J=4.0 Hz, 1H), 8.77 (d, J=4.0 Hz, 1H), 8.36 (d, J=4.0 Hz, 1H), 8.20 (m, 2H), 7.66 (d, J=4.0 Hz, 1H), 7.47 (m, 1H), 7.24 (s, 1H), 0.93 (m, 6H); MS: 343.0 (M+H$^+$).

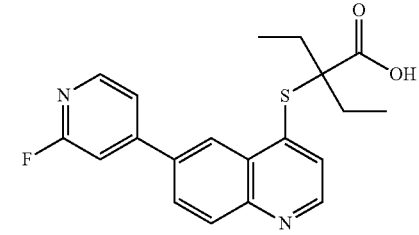

Product 118 (2-(6-(2-fluoropyridin-4-yl)-quinolin-4-ylthio)-2-ethylbutanoic acid): $^1$H NMR (DMSO, 400 MHz): δ (ppm): 12.96 (s, 1H), 8.87 (d, J=4.0 Hz, 1H), 8.74 (d, J=4.0

Hz, 1H), 8.33 (d, J=4.0 Hz, 1H), 8.18 (m, 2H), 7.64 (d, J=4.0 Hz, 1H), 7.44 (m, 1H), 7.24 (s, 1H), 3.94 (s, 3H), 1.89 (m, 4H), 0.91 (m, 6H); MS: 371.0 (M+H⁺).

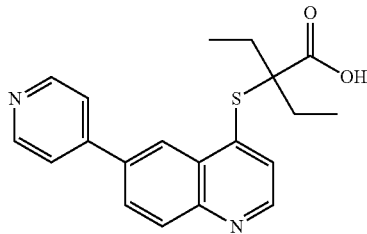

119

Product 119 (2-(6-(pyridin-4-yl)quinolin-4-ylthio)-2-ethylbutanoic acid): ¹H NMR (DMSO, 400 MHz): δ (ppm): 13.00 (s, 1H), 8.90 (d, J=8.0 Hz, 1H), 8.72 (m, 3H), 8.21 (m, 2H), 7.86 (m, 2H), 7.67 (d, J=4.0 Hz, 1H), 1.93 (m, 4H), 1.58 (m, 6H); MS: 353.1 (M+H⁺).

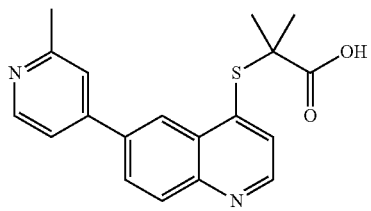

120

Product 120 (2-(6-(2-methylpyridin-4-yl)quinolin-4-ylthio)-2-methylpropanoic acid): 13.03 (s, 1H), 8.87 (d, J=4.0 Hz, 1H), 8.74 (d, J=4.0 Hz, 1H), 8.33 (d, J=4.0 Hz, 1H), 8.18 (m, 2H), 7.64 (d, J=4.0 Hz, 1H), 7.44 (m, 1H), 7.24 (s, 1H), 2.71 (s, 3H), 1.52 (m, 6H); MS: 339.1 (M+H⁺).

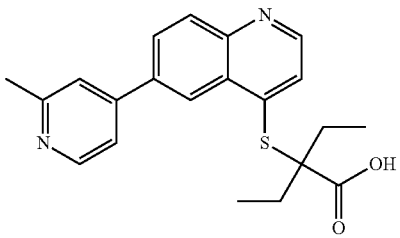

121

Product 121 (2-(6-(2-methylpyridin-4-yl)-quinolin-4-ylthio)-2-ethylbutanoic acid): ¹H NMR (DMSO, 400 MHz): δ (ppm): 12.99 (s, 1H), 8.85 (d, J=4.0 Hz, 1H), 8.77 (d, J=4.0 Hz, 1H), 8.35 (d, J=4.0 Hz, 1H), 8.15 (m, 2H), 7.69 (d, J=4.0 Hz, 1H), 7.47 (m, 1H), 7.26 (s, 1H), 3.94 (s, 3H), 1.92 (m, 4H), 0.9 (m, 6H); MS: 367.1 (M+H⁺).

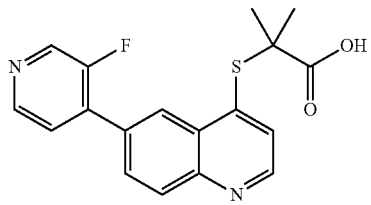

122

Product 122 (2-(6-(3-fluoropyridin-4-yl)-quinolin-4-ylthio)-2-methylpropanoic acid): MS: 343.1 (M+H⁺).

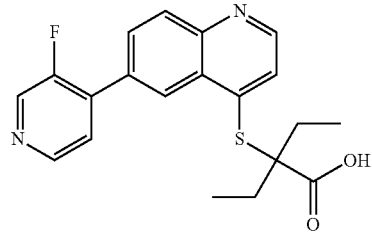

123

Product 123 (2-(6-(3-fluoropyridin-4-yl)-quinolin-4-ylthio)-2-ethylbutanoic acid): MS: 371.1 (M+H⁺).

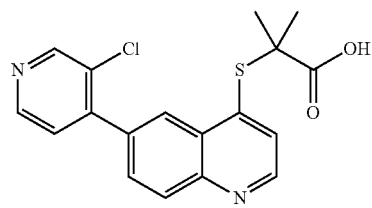

124

Product 124 (2-(6-(3-chloropyridin-4-yl)-quinolin-4-ylthio)-2-methylpropanoic acid): MS: 359.0 (M+H⁺).

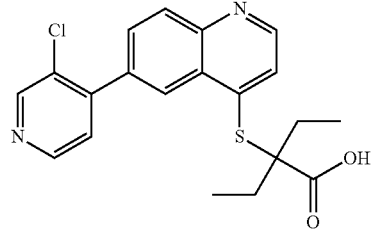

125

Product 125 (2-(6-(3-chloropyridin-4-yl)-quinolin-4-ylthio)-2-ethylbutanoic acid (125): MS: 387.0 (M+H⁺).

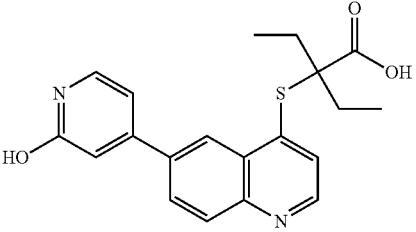

126

Product 126 (2-(6-(2-hydroxypyridin-4-yl)-quinolin-4-ylthio)-2-ethylbutanoic acid): MS: 369.0 (M+H⁺).

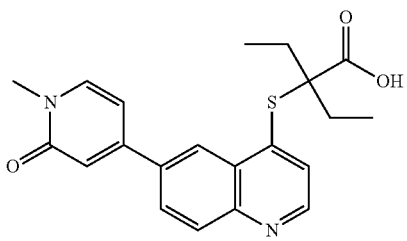

Product 127 (2-(6-(1-methyl-2-oxo-1,2-dihydropyridin-4-yl)-quinolin-4-ylthio)-2-ethylbutanoic acid (127): MS: 383.0 (M+H⁺).

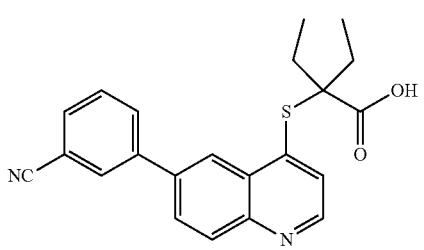

Product 138 (2-(6-(3-cyano-phenyl)-quinolin-4-ylthio)-2-ethylbutanoic acid): MS: 377.1 (M+H⁺).

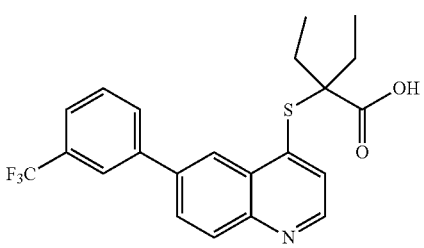

Product 139 (2-(6-(3-trifluoromethyl-phenyl)-quinolin-4-ylthio)-2-ethylbutanoic acid (139): MS: 420.1 (M+H⁺).

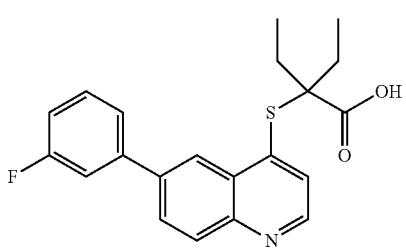

Product 140 (2-(6-(3-fluoro-phenyl)-quinolin-4-ylthio)-2-ethylbutanoic acid): MS: 370.1 (M+H⁺).

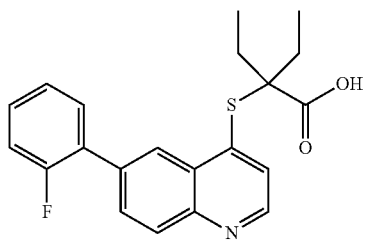

Product 141 (2-(6-(2-fluoro-phenyl)-quinolin-4-ylthio)-2-ethylbutanoic acid): MS: 370.1 (M+H⁺).

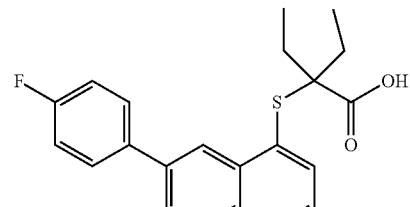

Product 142 (2-(6-(4-fluoro-phenyl)-quinolin-4-ylthio)-2-ethylbutanoic acid): MS: 370.1 (M+H⁺).

Example 2 Biological Assay of Compounds According to the Present Invention

Test example: Determination of the inhibitory activity of compounds according to the present invention against URAT1

Experimental Materials
- FBS (Invitrogen, Cat. No. 10099141)
- Trypsin (Invitrogen, Cat. No. 25200056)
- DPBS (Invitrogen, Cat. No. 14190250)
- DMEM (Invitrogen, Cat. No. 10564)
- Penicillin-Streptomycin (Invitrogen, Cat. No. 15070-063)
- TransIT-293 Transfection Reagent (MIRUS BIO, Cat. No. MIR2706)
- Opti-MEM® I Reduced Serum Medium (Invitrogen, Cat. No. 31985-070)
- URAT1 plasmid (Genecopoeia, Cat. No. EX-T4563-M03)
- Uric acid [8-14C] (ARC, Cat. No. ARC0513-250UCI)
- Ultima Gold™ XR (PerkinElmer, Cat. No. 6013111)
- Benzbromarone (J&K Scientific, Cat. No. 3562-84-3)
- D-Gluconic acid sodium salt (Aladdin, Cat. No. 527-07-1)
- Potassium D-gluconate (Aladdin, Cat. No. 299-27-4)
- Calcium gluconate (Aladdin, Cat. No. 299-28-5)
- DMSO (Sigma, Cat. No. D2650)
- Tube, 15 ml (Greiner, Cat. No. 07030115)
- Tube, 50 ml (BD Falcon, Cat. No. 352098)
- Poly-D-lysine 96-well microplates (BD, Cat. No. 356461)
- Isoplate-96 Microplate (PERKIN ELMER, Cat. No. 6005040)

Experimental Method:
Buffer Preparation

| Cl— free HBSS buffer solution | Cell lysate |
|---|---|
| 125 mM Sodium gluconate | 100 mM NaOH |

4.8 mM Potassium gluconate
1.3 mM Calcium gluconate
1.2 mM $KH_2PO_4$
1.2 mM $MgSO_4$
5.6 mM Glucose
25 mM HEPES (pH 7.4)

Cell Culture:
1. The HEK-293t cells that expressed the stable expression of hURAT1 were cultured in DMEM medium containing 10% FBS and 1% P/S, and incubated overnight in the incubator at 37° C. under 5% carbon dioxide.
2. the culture medium was removed, and the cells were washed with PBS, and then the pancreatin was added to digest for 2 minutes. After the cell is separated from the dish, 10 ml of medium was added to terminate digestion.
3. The cells were placed into a centrifugal apparatus and centrifugated for 2 minutes at the speed of 1000 rpm, followed by the addition of fresh 10 mL medium to resuspend the cells, and calculate the number of cells. The number of cells was adjusted to $4\times10^5$ cells/mL.
4. the above counted cells were inoculated into the 96-well plate at 100 μL/well.
5. The 96-well plate with inoculated cells was placed in a 37° C. cell incubator and cultivated overnight.

The uric acid absorption experiment labeled with isotope C14:
1. 5 mL of Cl-free HBSS buffer was added to a 15 mL centrifuge tube, followed by the addition of the uric acid labeled with C14, and the concentration of uric acid was 2 uCi/ml.
2. The medium in the 96-well plate that was previously cultivated overnight was removed, and the plate was washed three times with 100 mL preheated Cl-free HBSS buffer.
3. The buffer in the well-washed 96-well plate was removed.
4. 50 mL Cl-free HBSS buffer containing C-14 labeled uric acid was added into each well in the cleaned 96-well plate, and then DMSO solution of the compound that needs to be tested was added.
5. After the 96-well plate stood for 5 minutes at room temperature, all the liquid in it was removed.
6. 100 mL precooled Cl-free HBSS buffer was added to wash the plate three times.
7. After the remained liquid in the plates was completely removed, 50 μL cell lysis was added to each well, and the plate was agitated on the mixer at a speed of 600 revolutions/min for 10 minutes.
8. After 50 μL Ultima Gold™ XR scitillation cocktail fluid was added, the plate was continued to agitate for 10 minutes. The well-agitated plate was sealed, and the data was read on MicroBeta Trilux.
9. The test compound was dissolved in DMSO, and DMSO at the same concentration was added to the HEK293/hURAT1 cell well without test compounds. The uric acid uptake of cells at each test concentration was expressed as the average percentage inhibition ratio, comparable to the control DMSO. The radiation value obtained from the well containing DMSO is considered to be 100% of the cell uptake. The $IC_{50}$ values of compounds can be calculated by the inhibition rate at different concentrations.

The $IC_{50}$ values (nM) of hURAT1 inhibitory activity for compounds according to the present invention are shown in table 1. Among them, reference compound 1 was synthesized according to the method described in patent WO 2011/159839 A2. Reference compound 2 and reference compound 3 were synthesized according to the method described in patent WO 2014/183555 A1, and they were head-to-head tested with compounds 83 and 129 respectively under the same conditions. The $IC_{50}$ values of the reference compound 2 and compound 83 are the average of the multiple head-to-head comparison tests. The $IC_{50}$ values of the reference compound 3 and 129 are the average of two comparison tests.

TABLE 1

| Compound No. | Structure | $IC_{50}$ (nM) |
|---|---|---|
| Ref cpd 1 (RDEA3170) | 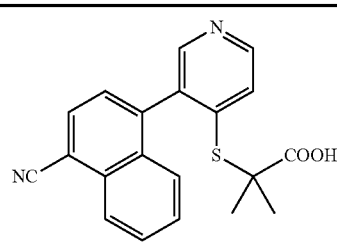 | 153.8 |
| Ref Cpd 2 | 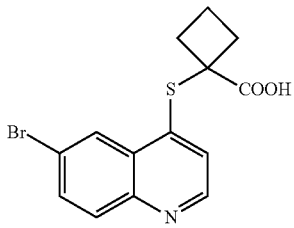 [SMILES: O=C(O)C1(Sc2ccnc3ccc(Br)cc23)CCC1] | 137.7 |

TABLE 1-continued

| Compound No. | Structure | IC$_{50}$ (nM) |
| --- | --- | --- |
| Ref Cpd 3 | 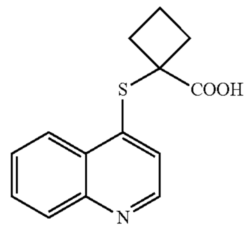 [SMILES: O=C(O)C1(Sc2ccnc3ccccc23)CCC1] | 794 |
| 1 | 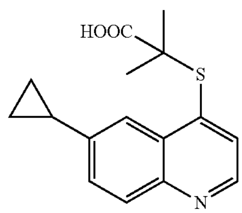 [SMILES: CC(C)(Sc1ccnc2ccc(C3CC3)cc12)C(=O)O] | 486 |
| 3 | 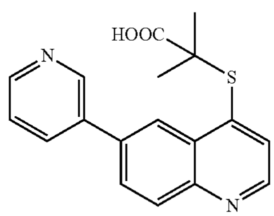 [SMILES: CC(C)(Sc1ccnc2ccc(-c3cccnc3)cc12)C(=O)O] | 514 |
| 4 | 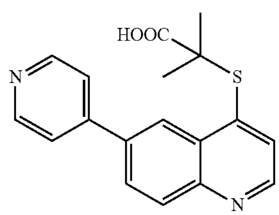 [SMILES: CC(C)(Sc1ccnc2ccc(-c3ccncc3)cc12)C(=O)O] | 127 |
| 19 | 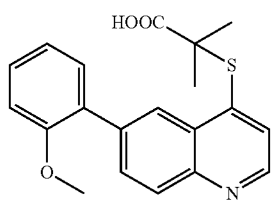 [SMILES: COc1ccccc1-c1ccc2nccc(SC(C)(C)C(=O)O)c2c1] | 472 |
| 20 | 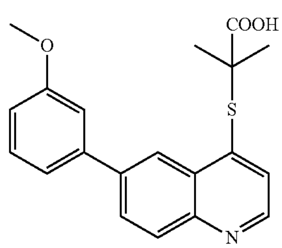 [SMILES: COc1cccc(-c2ccc3nccc(SC(C)(C)C(=O)O)c3c2)c1] | 21 |
| 21 | 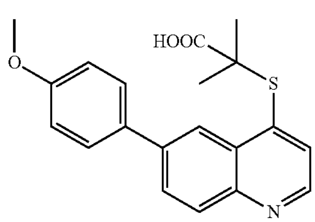 [SMILES: COc1ccc(-c2ccc3nccc(SC(C)(C)C(=O)O)c3c2)cc1] | 1896 |

TABLE 1-continued

| Compound No. | Structure | IC$_{50}$ (nM) |
|---|---|---|
| 24 | 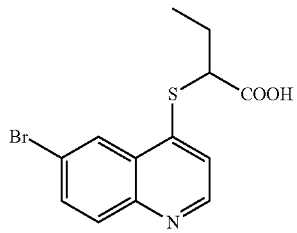 [SMILES: CCC(Sc1ccnc2ccc(Br)cc12)C(=O)O] | 6000 |
| 22 | 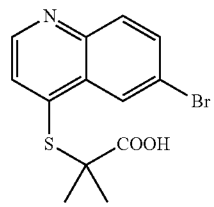 [SMILES: CC(C)(Sc1ccnc2ccc(Br)cc12)C(=O)O] | 159 |
| 25 | 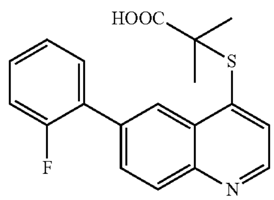 [SMILES: CC(C)(Sc1ccnc2ccc(-c3ccccc3F)cc12)C(=O)O] | 812 |
| 96 | 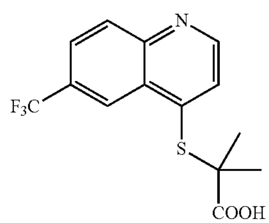 [SMILES: CC(C)(Sc1ccnc2ccc(C(F)(F)F)cc12)C(=O)O] | 772 |
| 83 | 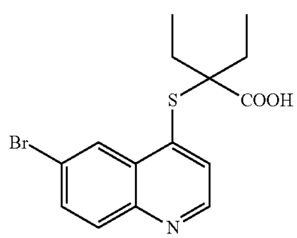 [SMILES: CCC(CC)(Sc1ccnc2ccc(Br)cc12)C(=O)O] | 70.6 |
| 129 | 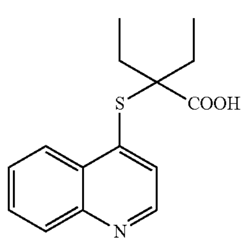 [SMILES: CCC(CC)(Sc1ccnc2ccccc12)C(=O)O] | 201 |
| 93 | 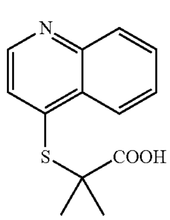 [SMILES: CC(C)(Sc1ccnc2ccccc12)C(=O)O] | 2400 |

TABLE 1-continued

| Compound No. | Structure | IC$_{50}$ (nM) |
|---|---|---|
| 114 | 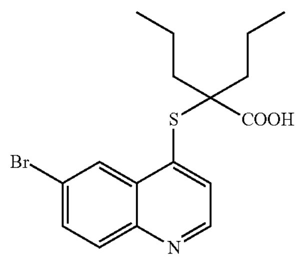 [SMILES: CCCC(CCC)(Sc1ccnc2ccc(Br)cc12)C(=O)O] | 203 |
| 117 | 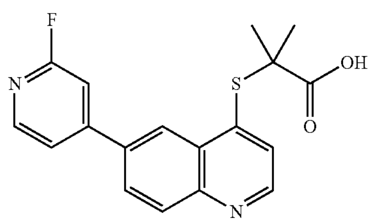 [SMILES: CC(C)(Sc1ccnc2ccc(-c3ccnc(F)c3)cc12)C(=O)O] | 272 |
| 118 | 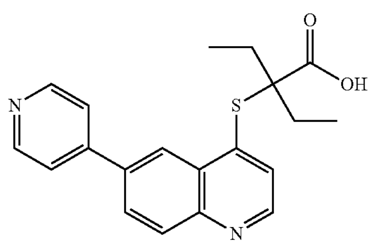 [SMILES: CCC(CC)(Sc1ccnc2ccc(-c3ccncc3)cc12)C(=O)O] | 36 |
| 105 | 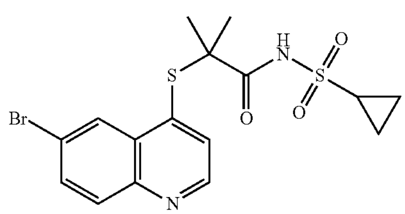 [SMILES: CC(C)(Sc1ccnc2ccc(Br)cc12)C(=O)NS(=O)(=O)C1CC1] | 1779 |
| 106 | 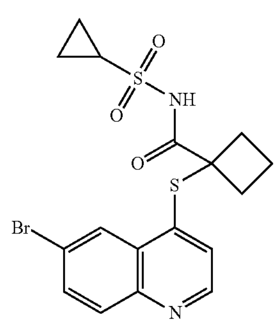 [SMILES: O=C(NS(=O)(=O)C1CC1)C1(Sc2ccnc3ccc(Br)cc23)CCC1] | 235 |
| 37 | 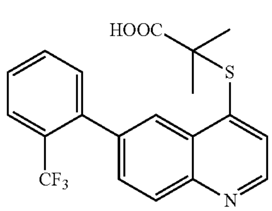 [SMILES: CC(C)(Sc1ccnc2ccc(-c3ccccc3C(F)(F)F)cc12)C(=O)O] | 325 |

TABLE 1-continued

| Compound No. | Structure | IC$_{50}$ (nM) |
|---|---|---|
| 100 | 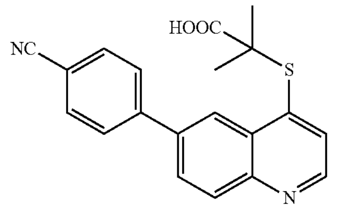 [SMILES: CC(C)(Sc1ccnc2ccc(-c3ccc(C#N)cc3)cc12)C(=O)O] | 8140 |
| 101 | 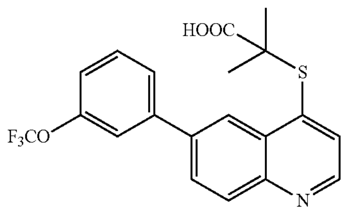 [SMILES: CC(C)(Sc1ccnc2ccc(-c3cccc(OC(F)(F)F)c3)cc12)C(=O)O] | 710 |
| 28 | 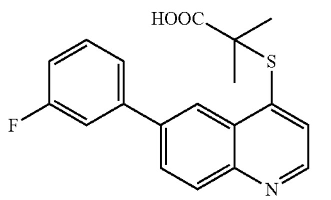 [SMILES: CC(C)(Sc1ccnc2ccc(-c3cccc(F)c3)cc12)C(=O)O] | 351 |
| 34 | 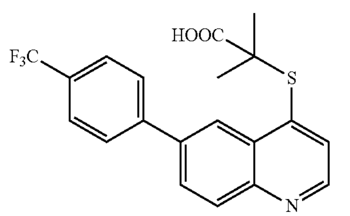 [SMILES: CC(C)(Sc1ccnc2ccc(-c3ccc(C(F)(F)F)cc3)cc12)C(=O)O] | 4600 |
| 37 | 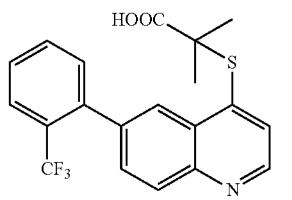 [SMILES: CC(C)(Sc1ccnc2ccc(-c3ccccc3C(F)(F)F)cc12)C(=O)O] | 325 |
| 115 | 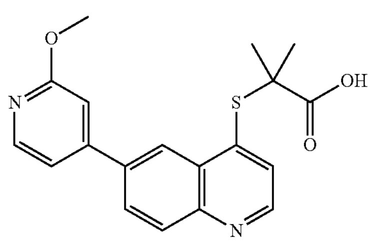 [SMILES: COc1cc(-c2ccc3nccc(SC(C)(C)C(=O)O)c3c2)ccn1] | 79 |
| 116 | 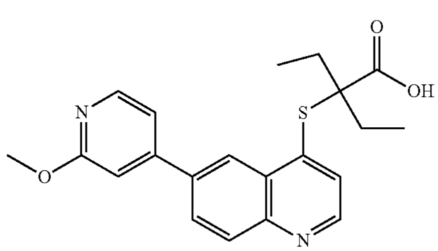 [SMILES: CCC(CC)(Sc1ccnc2ccc(-c3ccnc(OC)c3)cc12)C(=O)O] | 98 |

TABLE 1-continued

| Compound No. | Structure | IC$_{50}$ (nM) |
|---|---|---|
| 107 | 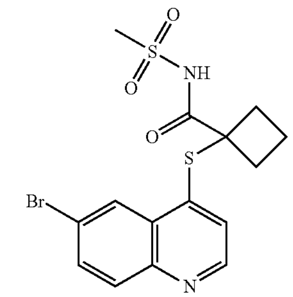 [SMILES: CS(=O)(=O)NC(=O)C1(Sc2ccnc3ccc(Br)cc23)CCC1] | 336 |
| 94 | 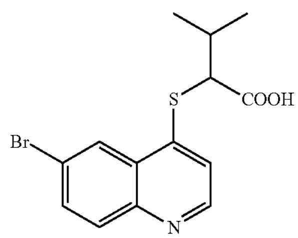 [SMILES: CC(C)C(Sc1ccnc2ccc(Br)cc12)C(=O)O] | 4300 |
| 95 | 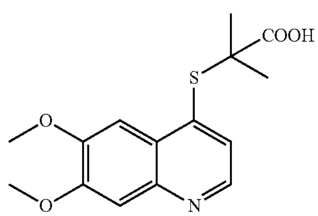 [SMILES: COc1cc2nccc(SC(C)(C)C(=O)O)c2cc1OC] | >30000 |
| 128 | 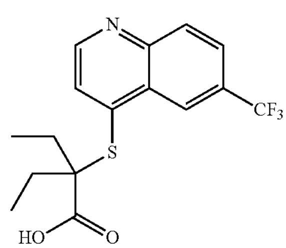 [SMILES: CCC(CC)(Sc1ccnc2ccc(C(F)(F)F)cc12)C(=O)O] | 74 |
| 109 | 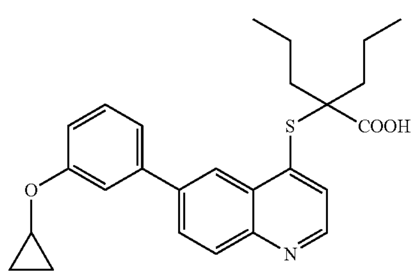 [SMILES: CCCC(CCC)(Sc1ccnc2ccc(-c3cccc(OC4CC4)c3)cc12)C(=O)O] | 722 |
| 110 | 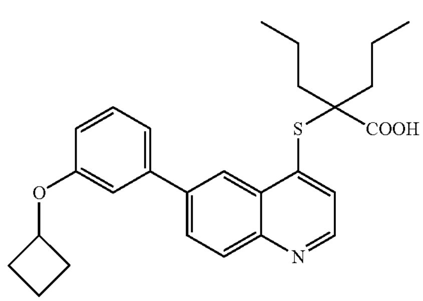 [SMILES: CCCC(CCC)(Sc1ccnc2ccc(-c3cccc(OC4CCC4)c3)cc12)C(=O)O] | 2858 |

TABLE 1-continued

| Compound No. | Structure | IC$_{50}$ (nM) |
|---|---|---|
| 102 | 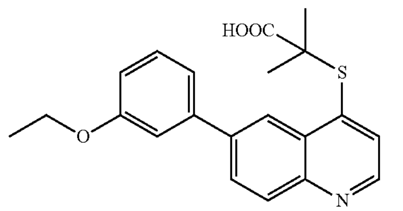 [SMILES: CCOc1cccc(-c2ccc3nccc(SC(C)(C)C(=O)O)c3c2)c1] | 32 |
| 103 | 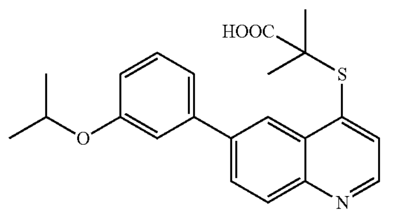 [SMILES: CC(C)Oc1cccc(-c2ccc3nccc(SC(C)(C)C(=O)O)c3c2)c1] | 37 |
| 104 | 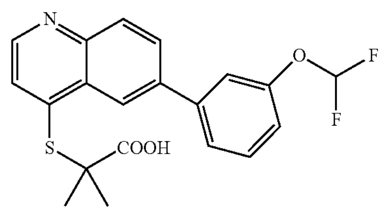 [SMILES: CC(C)(Sc1ccnc2ccc(-c3cccc(OC(F)F)c3)cc12)C(=O)O] | 238 |
| 108 | 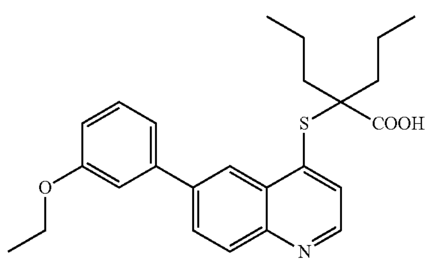 [SMILES: CCCC(CCC)(Sc1ccnc2ccc(-c3cccc(OCC)c3)cc12)C(=O)O] | 523 |
| 112 | 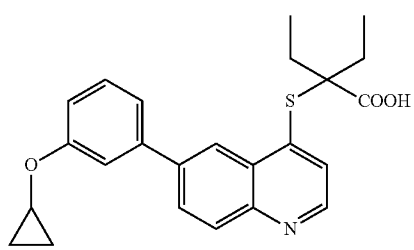 [SMILES: CCC(CC)(Sc1ccnc2ccc(-c3cccc(OC4CC4)c3)cc12)C(=O)O] | 147 |
| 113 | 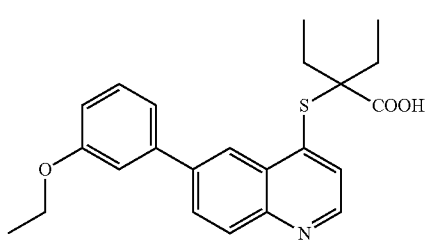 [SMILES: CCOc1cccc(-c2ccc3nccc(SC(CC)(CC)C(=O)O)c3c2)c1] | 109 |

TABLE 1-continued

| Compound No. | Structure | IC$_{50}$ (nM) |
|---|---|---|
| 119 | 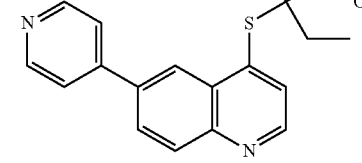 | 133 |
| 123 | 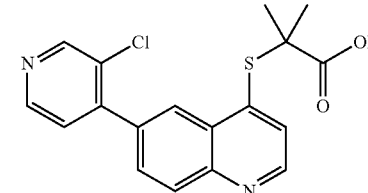 | 1400 |
| 111 | 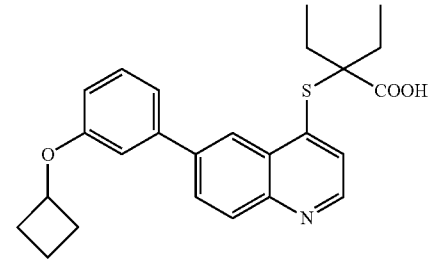 [SMILES: CCC(CC)(Sc1ccnc2ccc(-c3cccc(OC4CCC4)c3)cc12)C(=O)O] | 267 |
| 120 | 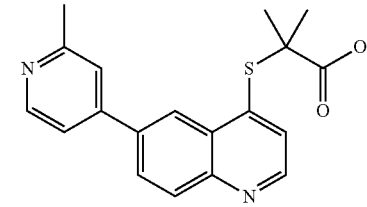 | 1235 |
| 121 | 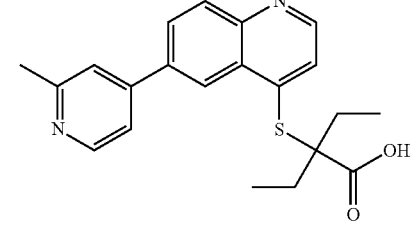 | 360 |

It can be seen from the above table that the compounds according to the present invention have an obvious inhibitory effect on uric acid transporter URAT1.

Reference compounds 1 and 2 are known to be high active inhibitors against uric acid transporter URAT1. Compound 83 showed a better inhibitory activity against the uric acid transporter than compound 1. Meanwhile, the statistical analysis on the activity data of compound 83 and the reference compound 2 obtained by multiple head to head tests is shown in table 2, and the results demonstrated that the activity of compound 83 was significantly different from that of reference compound 2. Combined with the structure and activity comparison of compound 129 and compounds 3, obviously, in the present invention, that the cycloalkyls at certain position of the compounds are substituted by ring-opened alkyl, especially the diethyl substituent, significantly increased the inhibitory activity of the compound against uric acid transporter URAT1.

TABLE 2

|  | Ref cpd2 (nM) | Cpd 83 (nM) |
|---|---|---|
| Multiple determination data | 72.9, 185, 172, 164, 144, 127, 99 | 42.5, 117, 89, 93, 56, 58, 38.9 |
| Average | 137.7 | 70.6 |
| SD | 29.3 | 26.6 |
| p values (Ref cpd 2) |  | 0.00008 |

Various compounds and salts, hydrates or solvates provided in the present invention are a uric acid reuptake inhibitor with higher selectivity than the typical compounds in this art. They can promote the uric acid excretion from the body and reduce serum uric acid to treat or prevent diseases characterized by abnormal uric acid levels. Amongst, the diseases are selected from the group of gout, recurrent gout symptoms, hyperuricemia, cardiovascular disease, Lesch-Nyhan syndrome, Kearns-Sayre Syndrome, kidney disease, arthritis, urinary stone disease, lead poisoning, hyperparathyroidism, psoriasis, sarcoidosis or hypoxanthine-guanine phosphoribosyl transferase deficiency, with a characteristic of, with an effect of reducing uric acid in animal and human body.

The invention claimed is:

1. A compound of formula (I) or optical isomers or solvates or pharmaceutically acceptable salts or pro-drugs thereof,

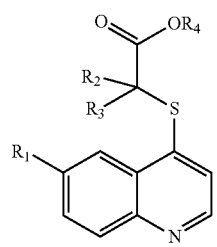

(I)

wherein, $R_1$ is selected from the group consisting of hydrogen, halogen, cyano, nitro, alkyl, alkenyl, alkynyl, cycloalkyl, heterocyclic radical, aryl, heteroaryl, —$OR^d$, —$S(O)_mR^d$, —$C(O)R^d$, $C(O)OR^d$, —$C(O)NR_eR^f$, —$NR^eR^f$, and $NR^eC(O)R^f$, in which said alkyl, alkenyl, alkynyl, cycloalkyl, heterocyclic radical, aryl or heteroaryl are independently and optionally further substituted by one or more substituents selected from the group consisting of halogen, cyano, nitro, oxo, alkyl, haloalkyl, hydroxyalkyl, alkenyl, alkynyl, cycloalkyl, heterocyclic radical, aryl, heteroaryl, —$OR^d$, —$S(O)_mR^d$, —$C(O)R^d$, $C(O)OR^d$, —$C(O)NR^eR^f$, —$NR^eR^f$, and $NR^eC(O)R^f$;

$R_2$ is hydrogen and $R_3$ is methyl;

or $R_2$ is hydrogen and $R_3$ is ethyl;

or, $R_2$ is hydrogen and $R_3$ is isopropyl;

or, $R_2$ and $R_3$ are independently selected from the group consisting of halogen, cyano, nitro, alkyl, alkenyl, alkynyl, cycloalkyl, heterocyclic radical, aryl, heteroaryl, —$OR^d$, —$S(O)_mR^d$, —$C(O)R^d$, $C(O)OR^d$, —$C(O)NR^eR^f$, —$NR^eR^f$, and $NR^eC(O)R^f$, wherein said alkyl, alkenyl, alkynyl, cycloalkyl, heterocyclic radical, aryl, or heteroaryl are independently and optionally further substituted by one or more substituents that are selected from the group consisting of halogen, cyano, nitro, oxo-, alkyl, haloalkyl, hydroxyalkyl, alkenyl, alkynyl, cycloalkyl, heterocyclic radical, aryl, heteroaryl, —$OR^d$, —$S(O)_mR^d$, —$C(O)R^d$, $C(O)OR^d$, —$C(O)NR^eR^f$, —$NR^eR^f$, and $NR^eC(O)R^f$;

$R^d$ is selected from the group consisting of hydrogen, halogen, alkyl, cycloalkyl, heterocyclic radical, aryl, and heteroaryl, wherein said alkyl, cycloalkyl, heterocyclic radical, aryl, or heteroaryl is independently and optionally further substituted by one or more substituents that are selected from the group consisting of halogen, cyano, nitro, hydroxyl, oxo-, alkyl, haloalkyl, hydroxyalkyl, alkoxy, cycloalkyl, heterocyclic radical, aryl, heteroaryl, carboxyl, carboxylic ester, —$C(O)NR^eR^f$, —$NR^eR^f$, and $NR^eC(O)R^f$;

$R^e$, $R^f$ are independently selected from the group consisting of hydrogen, alkyl, cycloalkyl, heterocyclic radical, aryl, and heteroaryl, wherein said alkyl, cycloalkyl, heterocyclic radical, aryl or heteroaryl are independently and optionally further substituted by one or more substituents selected from the group consisting of halogen, cyano, nitro, hydroxyl, oxo-, alkyl, haloalkyl, hydroxyalkyl, alkoxy, cycloalkyl, heterocyclic radical, aryl, heteroaryl, carboxyl, and carboxylic ester group; and m is 0, 1 or 2;

$R_4$ is selected from the group consisting of hydrogen, $C_1$-$C_6$ alkyl, and cycloalkyl, wherein said alkyl and cycloalkyl are independently and optionally substituted by one or more substituents selected from the group consisting of halogen, cyano, nitro, hydroxyl, oxo-, alkyl, haloalkyl, hydroxyalkyl, alkoxy, cycloalkyl, heterocyclic radical, aryl, heteroaryl, carboxyl, carboxylic ester group, —$C(O)NR^eR^f$, —$NR^eR^f$, and $NR^eC(O)R^f$.

2. The compound according to claim 1, wherein, $R_1$ is selected from the group consisting of halogen, substituted or unsubstituted alkyl, substituted or unsubstituted aryl, substituted or unsubstituted heteroaryl, and substituted or unsubstituted cycloalkyl, $R_2$ and $R_3$ are independently selected from the group consisting of halogen, substituted or unsubstituted alkyl, substituted or unsubstituted aryl, substituted or unsubstituted heteroaryl, and substituted or unsubstituted cycloalkyl, $R_4$ is hydrogen, $C_1$-$C_6$ alkyl, or $C_3$-$C_6$ cycloalkyl.

3. The compound according to claim 1, or optical isomers or solvates or pharmaceutically acceptable salts or pro-drugs thereof, wherein, $R_1$ is selected from the group consisting of halogen, substituted or unsubstituted aryl, substituted or unsubstituted pyridyl, substituted or unsubstituted pyrimidinyl, substituted or unsubstituted pyrrolyl, substituted or unsubstituted imidazolyl, substituted or unsubstituted furyl, substituted or unsubstituted thienyl, substituted or unsubstituted oxazolyl, substituted or unsubstituted thiazolyl, substituted or unsubstituted oxdiazolyl, substituted or unsubstituted thiadiazolyl, and $C_3$-$C_6$ cycloalkyl.

4. The compound according to claim 1, or optical isomers or solvates or pharmaceutically acceptable salts or pro-drugs thereof, wherein, $R_2$ and $R_3$ are independently halogen or $C_1$-$C_6$ alkyl.

5. The compound according to claim 4, or optical isomers or solvates or chemically pharmaceutically salts or pro-drugs thereof, wherein the compound has the structure of formula (Id) or (Ie):

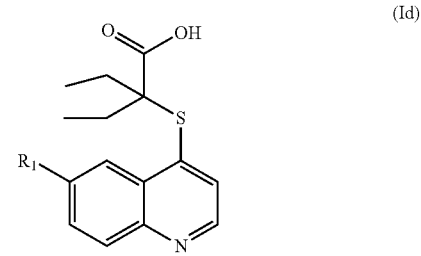

(Id)

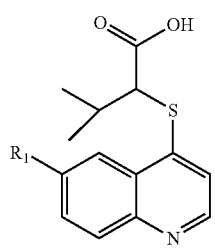
(Ie)

6. The compound according to claim 5, or optical isomers or solvates or pharmaceutically acceptable salts or pro-drugs thereof, wherein, $R_1$ is selected from the group consisting of halogen, trifluoromethyl, substituted or unsubstituted aryl, substituted or unsubstituted pyridyl, substituted or unsubstituted pyrimidinyl, substituted or unsubstituted pyrrolyl, substituted or unsubstituted imidazolyl, substituted or unsubstituted furyl, substituted or unsubstituted thienyl, substituted or unsubstituted oxazolyl, substituted or unsubstituted thiazolyl, substituted or unsubstituted oxdiazolyl, substituted or unsubstituted thiadiazolyl, and $C_3$-$C_6$ cycloalkyl.

7. The compound according to claim 1, or optical isomers or solvates or chemically acceptable salts or pro-drugs, that are selected from the group consisting of 1
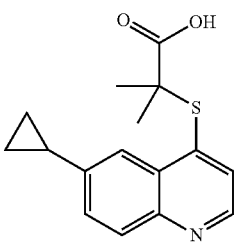

2
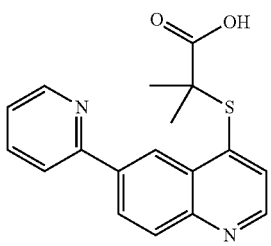

3
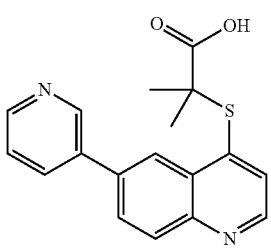

4
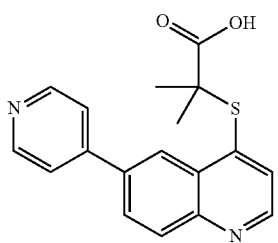

5
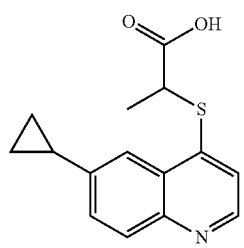

6
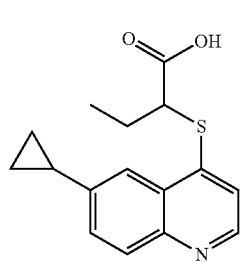

7
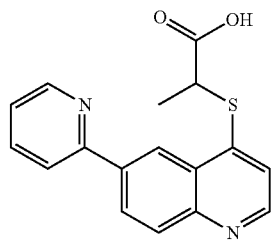

8
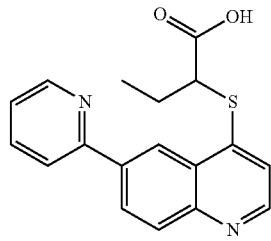

9
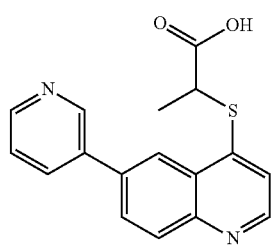

| | |
|---|---|
| 10 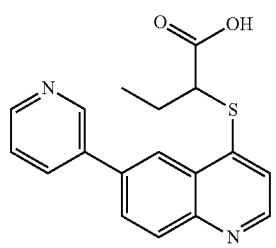 | 16 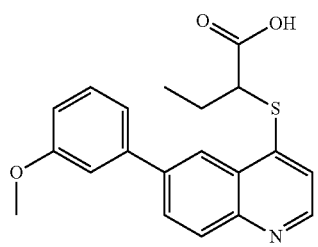 |
| 11 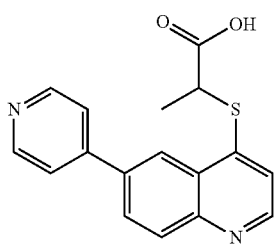 | 17 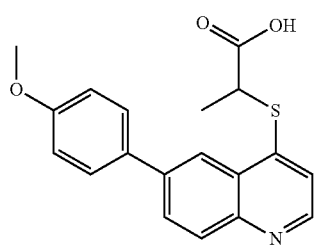 |
| 12 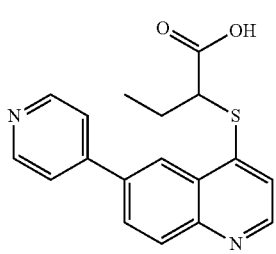 | 18 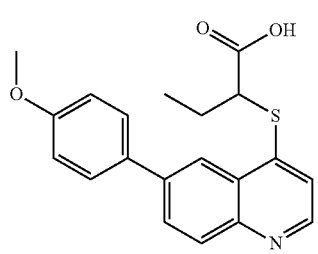 |
| 13 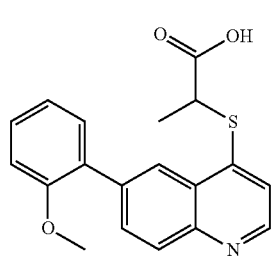 | 19 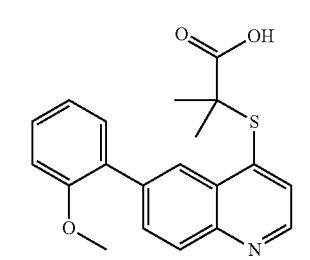 |
| 14 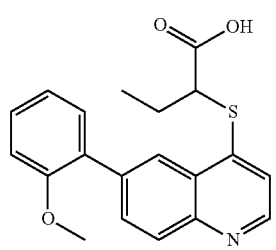 | 20 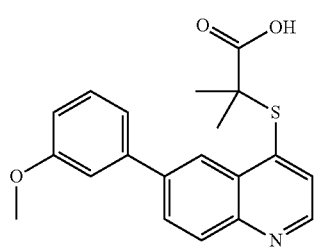 |
| 15 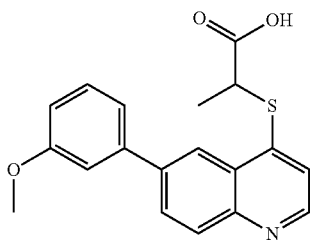 | 83 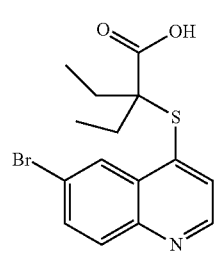 |

| | |
|---|---|
| 84 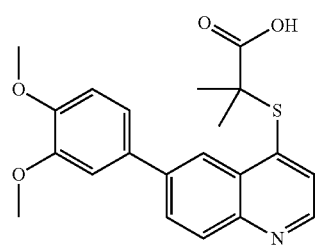 | 24 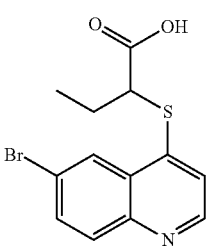 |
| 85 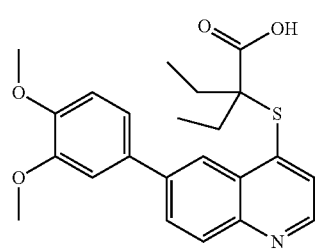 | 25 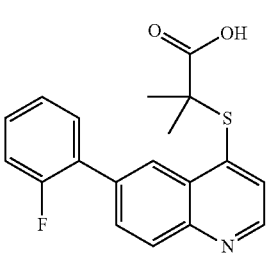 |
| 86 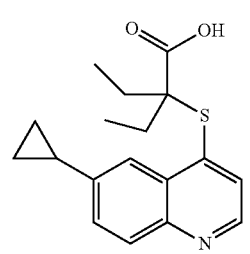 | 26 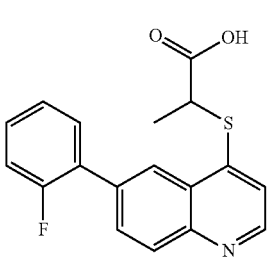 |
| 21 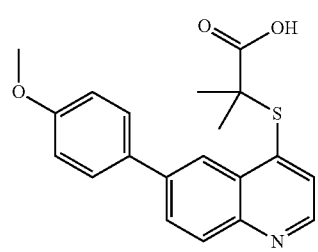 | 27 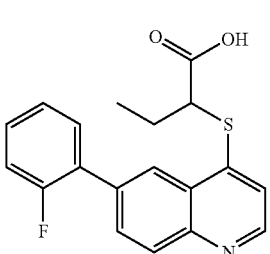 |
| 22 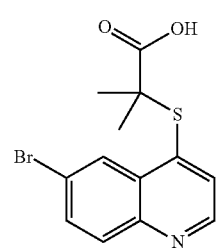 | 28 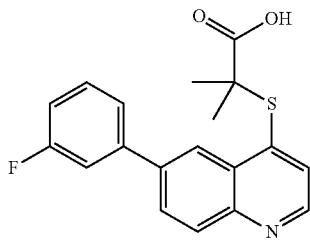 |
| 23 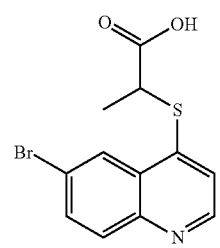 | 29 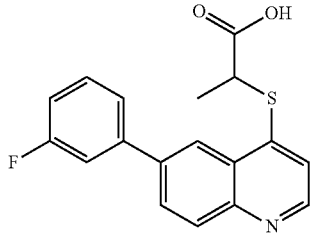 |

| | |
|---|---|
| 30 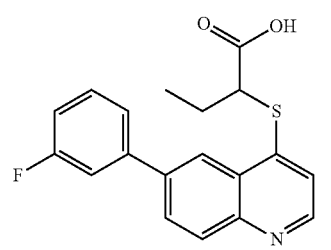 | 36 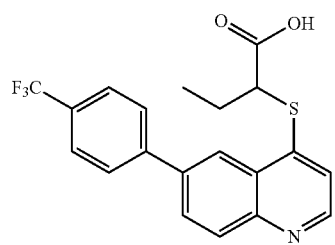 |
| 31 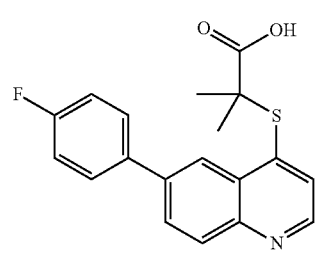 | 37 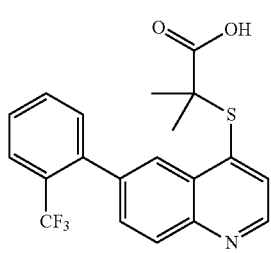 |
| 32 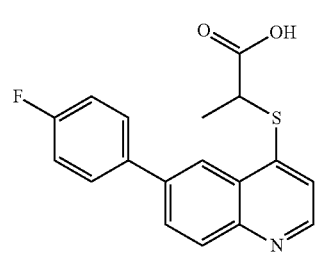 | 38 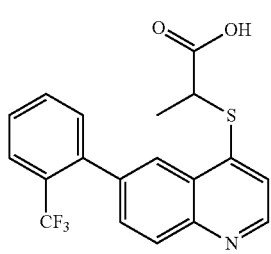 |
| 33 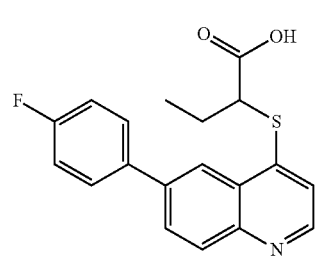 | 39 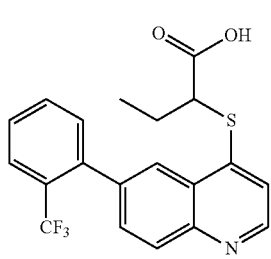 |
| 34 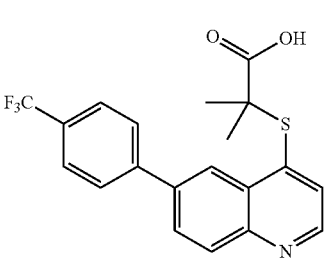 | 40 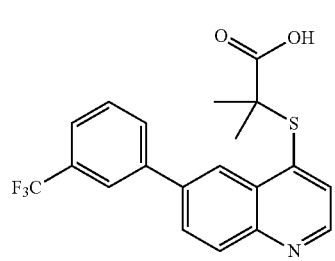 |
| 35 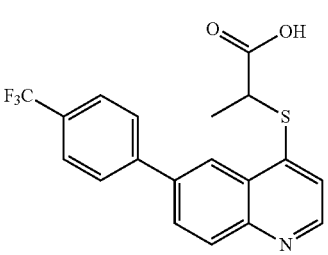 | 41 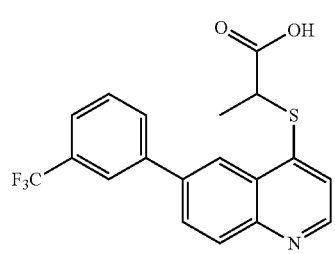 |

-continued
42
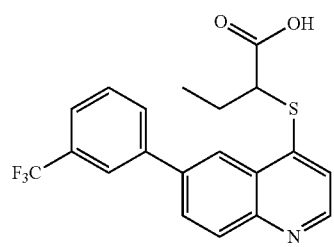
93
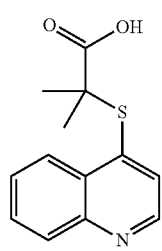
94
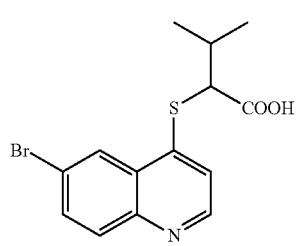
95
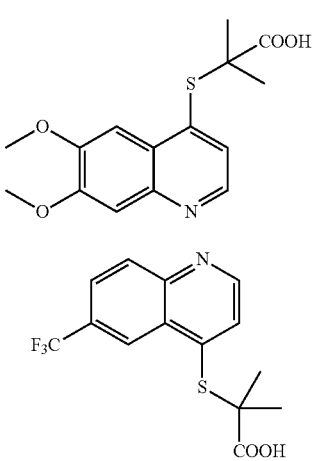
96
100
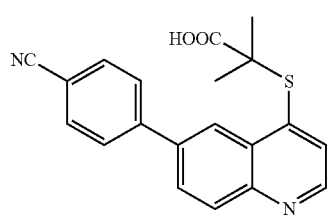
101
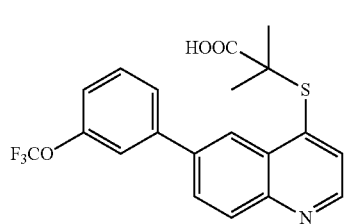
-continued
102
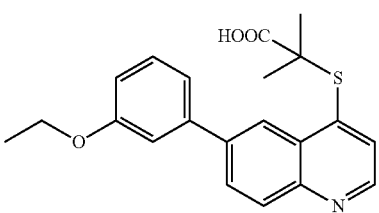
103
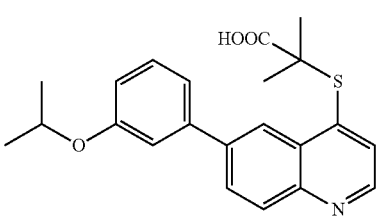
104
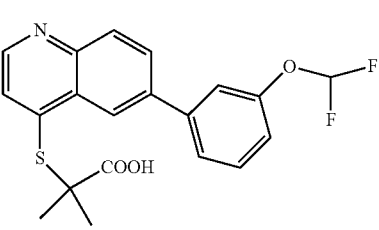
108
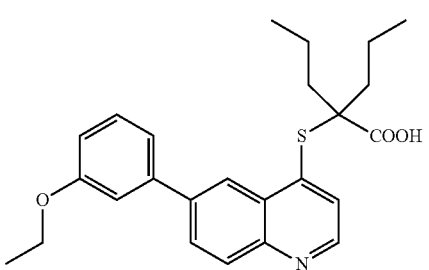
109
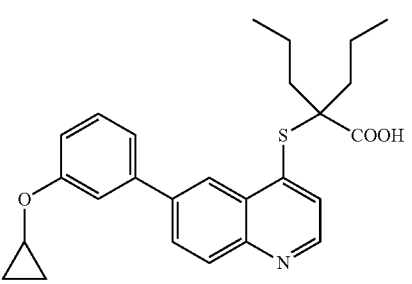
110
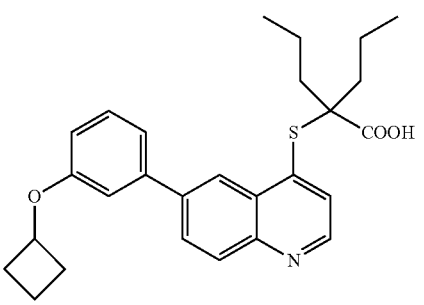

| 111 | 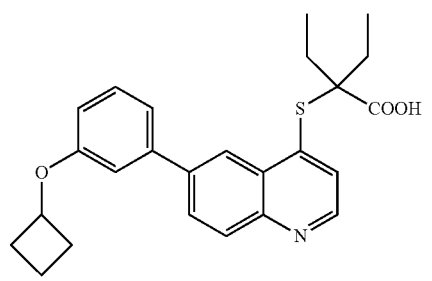 |
| 112 | 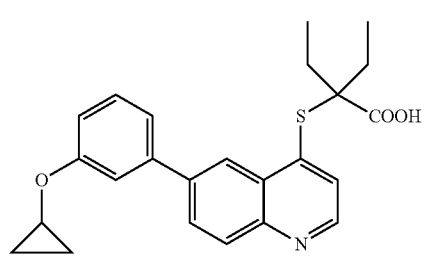 |
| 113 | 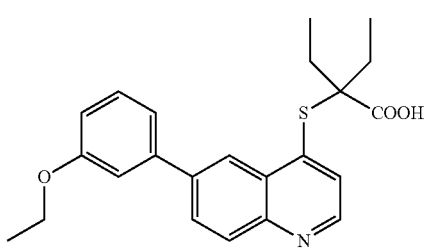 |
| 114 | 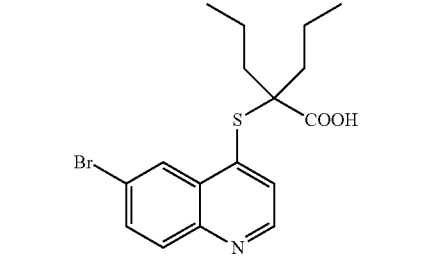 |
| 115 | 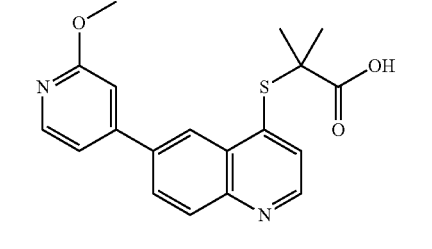 |
| 116 | 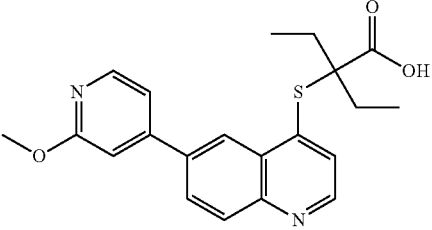 |
| 117 | 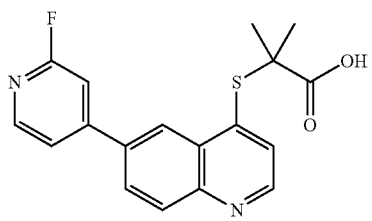 |
| 119 | 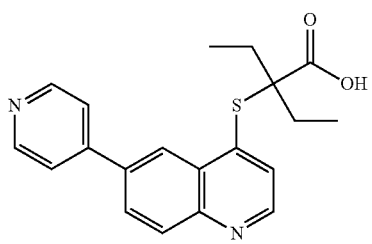 |
| 120 | 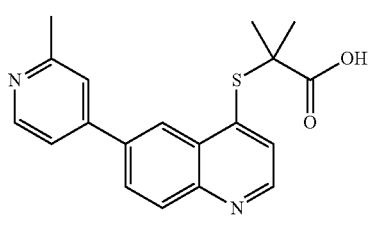 [SMILES: Cc1cc(-c2ccc3nccc(SC(C)(C)C(=O)O)c3c2)ccn1] |
| 118 | 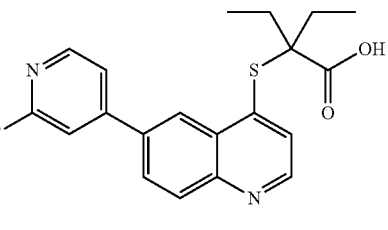 |
| 121 | 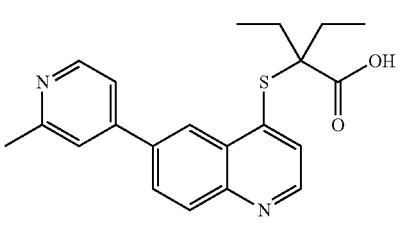 |
| 122 | 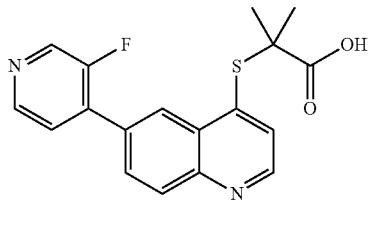 |
| 123 | 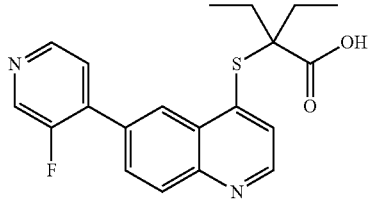 |

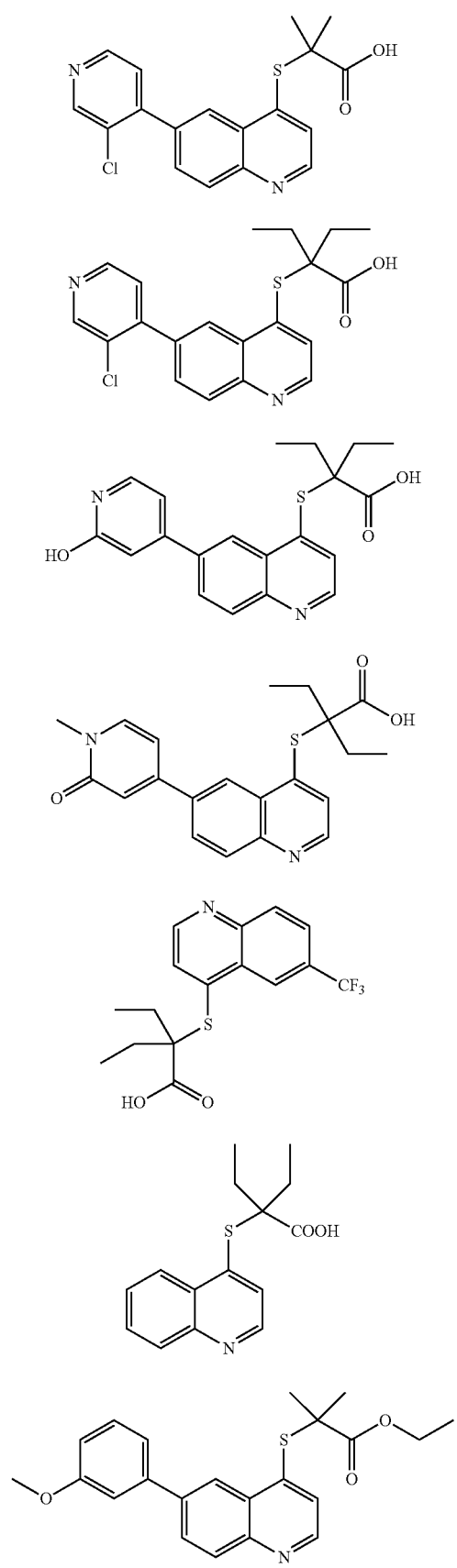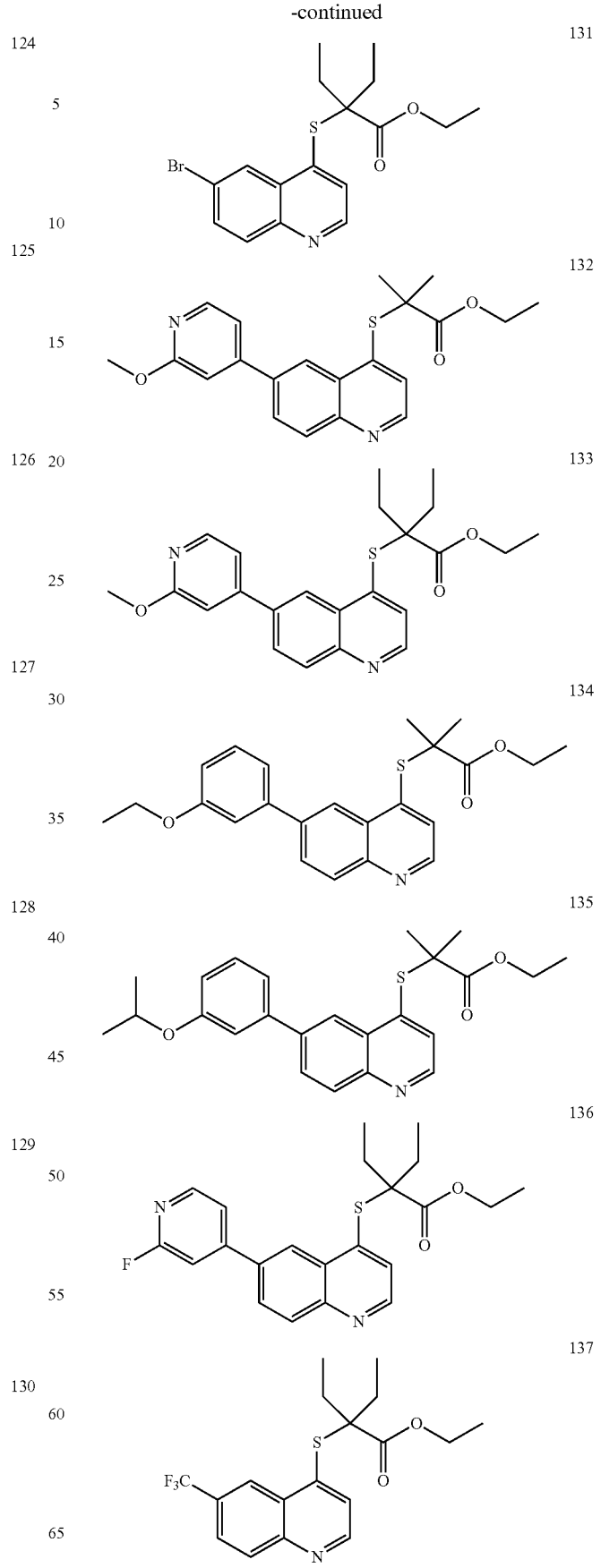

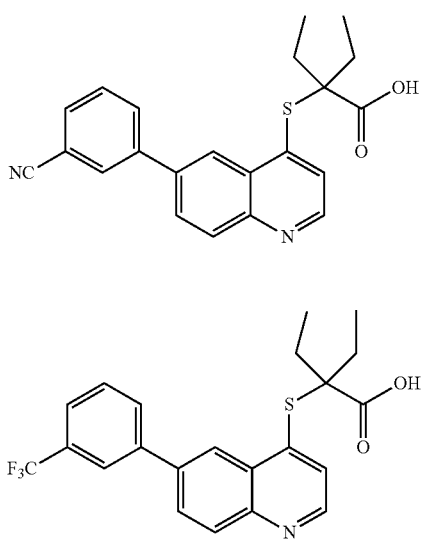

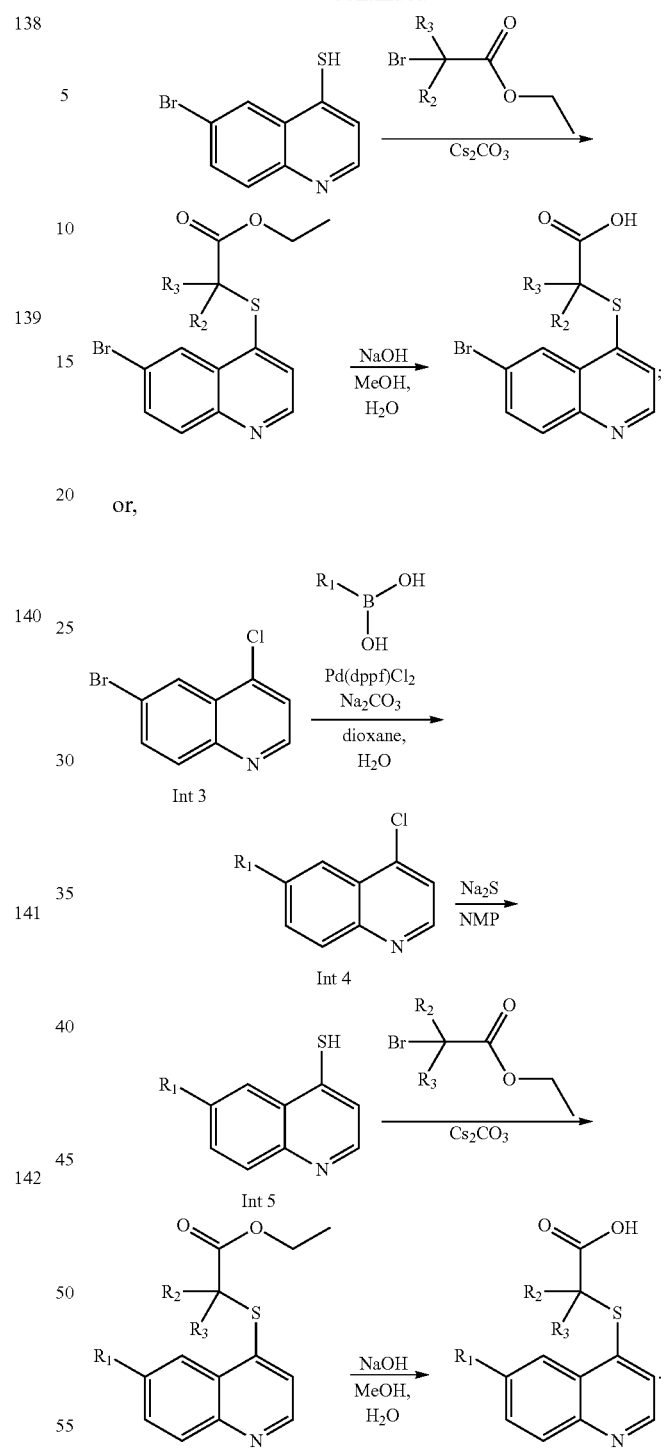

8. The method for preparation of compounds according to claim 1, comprising:

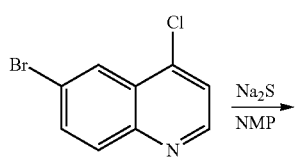

9. A method of treating abnormal uric acid levels, comprising administering the compound according to claim 1 or the optical isomer or the solvate or the pharmaceutically acceptable salt or the pro-drugs thereof to a patient in need thereof.

10. A method of treating diseases characterized by abnormal uric acid levels, wherein the diseases are selected from gout, gout attack, gouty arthritis and hyperuricemia, comprising administering a compound according to claim 1 or the optical isomer or the solvate or the pharmaceutically acceptable salt or the prodrug thereof to a patient in need thereof.

11. The compound according to claim 2, wherein $R_1$ is selected from the group consisting of F, Br, Cl, pyridyl, pyrimidinyl, pyrrolyl, imidazolyl, phenyl, trifluoromethyl, and cyclopropyl, wherein said phenyl is optionally further substituted by one or more substituents selected from the group consisting of methoxy, ethoxy, fluorine, chlorine, bromine, and trifluoromethyl.

12. The compound according to claim 4, wherein
$R_2$ and $R_3$ are both methyl;
or, $R_2$ and $R_3$ are both ethyl;
or, $R_2$ and $R_3$ are both n-propyl.

13. The compound according to claim 6, wherein $R_1$ is selected from the group consisting of F, Br, Cl, trifluoromethyl, pyridyl, pyrimidinyl, pyrrolyl, imidazolyl, phenyl, and cyclopropyl, wherein said phenyl is optionally further substituted by one or more substituents selected from the group consisting of methoxy, ethoxy, fluorine, chlorine, bromine, and trifluoromethyl, wherein the pharmaceutically acceptable salts thereof include the salts formed with bases, and sodium salt is preferable; further includes the salts formed with the pharmaceutically acceptable acids.

\* \* \* \* \*